(12) United States Patent
Klinman et al.

(10) Patent No.: US 8,466,116 B2
(45) Date of Patent: *Jun. 18, 2013

(54) USE OF CPG OLIGODEOXYNUCLEOTIDES TO INDUCE EPITHELIAL CELL GROWTH

(75) Inventors: Dennis M. Klinman, Potomac, MD (US); Takashi Sato, Yokohama (JP)

(73) Assignee: The Unites States of America as represented by the Secretary of the Department of Health and Human Services, Washington, DC (US)

( * ) Notice: Subject to any disclaimer, the term of this patent is extended or adjusted under 35 U.S.C. 154(b) by 966 days.

This patent is subject to a terminal disclaimer.

(21) Appl. No.: 12/205,756

(22) Filed: Sep. 5, 2008

(65) Prior Publication Data

US 2009/0099122 A1 Apr. 16, 2009

Related U.S. Application Data

(63) Continuation-in-part of application No. 10/499,597, filed as application No. PCT/US02/40955 on Dec. 19, 2002, now Pat. No. 7,615,227.

(60) Provisional application No. 60/970,145, filed on Sep. 5, 2007, provisional application No. 60/343,457, filed on Dec. 20, 2001.

(51) Int. Cl.
| | | |
|---|---|---|
| *A61K 39/00* | (2006.01) | |
| *A61K 39/38* | (2006.01) | |
| *A61K 45/00* | (2006.01) | |
| *A61K 47/00* | (2006.01) | |
| *A61K 48/00* | (2006.01) | |
| *A01N 43/04* | (2006.01) | |
| *C07H 21/02* | (2006.01) | |

(52) U.S. Cl.
USPC ............... 514/44 R; 424/184.1; 424/278.1; 424/198.1; 536/23.1

(58) Field of Classification Search
None
See application file for complete search history.

(56) References Cited

U.S. PATENT DOCUMENTS

| | | |
|---|---|---|
| 2,215,233 A | 9/1940 | Ruskin |
| 3,906,092 A | 9/1975 | Hilleman et al. |
| 3,911,117 A | 10/1975 | Ender |
| 3,914,450 A | 10/1975 | Robbins et al. |
| 4,469,863 A | 9/1984 | Ts'o et al. |
| 4,544,559 A | 10/1985 | Gil et al. |
| 4,741,914 A | 5/1988 | Kimizuka et al. |
| 4,758,553 A | 7/1988 | Ogoshi |
| 4,806,376 A | 2/1989 | Saeki et al. |
| 4,956,296 A | 9/1990 | Fahnestock |
| 4,963,387 A | 10/1990 | Nakagawa et al. |
| 4,994,442 A | 2/1991 | Gil et al. |
| 5,023,243 A | 6/1991 | Tullis |
| 5,066,500 A | 11/1991 | Gil et al. |
| 5,231,085 A | 7/1993 | Alexander et al. |
| 5,234,811 A | 8/1993 | Beutler et al. |
| 5,248,670 A | 9/1993 | Draper et al. |
| 5,268,365 A | 12/1993 | Rudolph et al. |
| 5,288,509 A | 2/1994 | Potman et al. |
| 5,488,039 A | 1/1996 | Masor et al. |
| 5,492,899 A | 2/1996 | Masor et al. |
| 5,585,479 A | 12/1996 | Hoke et al. |
| 5,591,721 A | 1/1997 | Agrawal et al. |
| 5,602,109 A | 2/1997 | Masor et al. |
| 5,612,060 A | 3/1997 | Alexander |
| 5,614,191 A | 3/1997 | Puri et al. |
| 5,650,156 A | 7/1997 | Grinstaff et al. |
| 5,663,153 A | 9/1997 | Hutcerson et al. |
| 5,679,397 A | 10/1997 | Kuroda et al. |
| 5,684,147 A | 11/1997 | Agrawal et al. |
| 5,700,590 A | 12/1997 | Masor et al. |
| 5,712,256 A | 1/1998 | Kulkarni et al. |
| 5,723,335 A | 3/1998 | Hutcerson et al. |
| 5,786,189 A | 7/1998 | Loct et al. |
| 5,804,566 A | 9/1998 | Carson et al. |
| 5,840,705 A | 11/1998 | Tsukada et al. |
| 5,849,719 A | 12/1998 | Carson et al. |
| 5,895,652 A | 4/1999 | Giampapa |
| 5,919,456 A | 7/1999 | Puri et al. |
| 5,922,766 A | 7/1999 | Acosta et al. |
| 5,976,580 A | 11/1999 | Ivey et al. |
| 5,980,958 A | 11/1999 | Naylor et al. |
| 5,994,126 A | 11/1999 | Steinman et al. |

(Continued)

FOREIGN PATENT DOCUMENTS

| | | |
|---|---|---|
| EP | 0 286 224 | 10/1988 |
| EP | 0 302 758 | 11/1989 |
| EP | 0 468 520 A2 | 1/1991 |
| EP | 0 092 574 | 4/1992 |
| EP | 0 572 735 A1 | 12/1993 |
| EP | 0 855 184 A1 | 7/1998 |
| EP | 1 198 249 | 4/2002 |
| WO | WO 91/12811 | 9/1991 |
| WO | WO 92/03456 | 4/1992 |
| WO | WO 92/18522 | 10/1992 |

(Continued)

OTHER PUBLICATIONS

Blazar et al. Blood 2001, 98:1217-1225.*
Takeshita et al. The Journal of Immunology, 2001, 167:3555-3558.*
U.S. 6,008,200, 12/1999, (withdrawn).
Adya, et al., "Expansion of CREB's DNA recognition specificity by Tax results from interaction with Ala-Ala-Arg at positions 282-284 near the conserved DNA-binding domain of CREB". Proc. Natl. Acad. Sci. USA 91(12):5642-5646 (1994).

(Continued)

*Primary Examiner* — Oluwatosin Ogunbiyi
(74) *Attorney, Agent, or Firm* — Klarquist Sparkman, LLP

(57) ABSTRACT

This disclosure provides a method of inducing epithelial cell growth. The method includes administering an effective amount of a K-type CpG oligonucleotide, thereby inducing epithelial cell growth. The epithelial cell can be in vivo or in vitro. Methods are also provided for inducing wound healing in a subject. The methods include administering to the subject a therapeutically effective amount of at least one K-type CpG ODN.

44 Claims, 11 Drawing Sheets

U.S. PATENT DOCUMENTS

| | | | |
|---|---|---|---|
| 6,022,853 | A | 2/2000 | Kuberasampath et al. |
| 6,194,388 | B1 | 2/2001 | Krieg et al. |
| 6,207,646 | B1 | 3/2001 | Krieg et al. |
| 6,214,806 | B1 | 4/2001 | Krieg et al. |
| 6,218,371 | B1 | 4/2001 | Krieg et al. |
| 6,239,116 | B1 | 5/2001 | Krieg et al. |
| 6,339,068 | B1 | 1/2002 | Krieg et al. |
| 6,406,705 | B1 | 6/2002 | Davis et al. |
| 6,423,539 | B2 | 7/2002 | Fong et al. |
| 6,428,788 | B1 | 8/2002 | Debinski et al. |
| 6,429,199 | B1 | 8/2002 | Krieg et al. |
| 6,498,148 | B1 | 12/2002 | Raz |
| 6,514,948 | B1 | 2/2003 | Raz et al. |
| 6,534,062 | B2 | 3/2003 | Raz et al. |
| 6,552,006 | B2 | 4/2003 | Raz et al. |
| 6,562,798 | B1 | 5/2003 | Schwartz |
| 6,589,940 | B1 | 7/2003 | Raz et al. |
| 6,610,661 | B1 | 8/2003 | Carson et al. |
| 6,613,751 | B2 | 9/2003 | Raz et al. |
| 6,653,292 | B1 | 11/2003 | Krieg et al. |
| 2001/0034330 | A1 | 10/2001 | Kensil |
| 2001/0036462 | A1 | 11/2001 | Fong et al. |
| 2001/0044416 | A1 | 11/2001 | McCluskie et al. |
| 2001/0046967 | A1 | 11/2001 | Van Nest |
| 2002/0006403 | A1 | 1/2002 | Yu et al. |
| 2002/0028784 | A1 | 3/2002 | Van Nest |
| 2002/0042383 | A1 | 4/2002 | Yew et al. |
| 2002/0042387 | A1 | 4/2002 | Raz et al. |
| 2002/0055477 | A1 | 5/2002 | Van Nest et al. |
| 2002/0064515 | A1 | 5/2002 | Krieg et al. |
| 2002/0065236 | A1 | 5/2002 | Yew et al. |
| 2002/0086295 | A1 | 7/2002 | Raz et al. |
| 2002/0086839 | A1 | 7/2002 | Raz et al. |
| 2002/0090724 | A1 | 7/2002 | Taylor et al. |
| 2002/0091095 | A1 | 7/2002 | Phillips et al. |
| 2002/0091097 | A1 | 7/2002 | Bratzler et al. |
| 2002/0098199 | A1 | 7/2002 | Van Nest et al. |
| 2002/0098205 | A1 | 7/2002 | Choi et al. |
| 2002/0098980 | A1 | 7/2002 | Choi et al. |
| 2002/0107212 | A1 | 8/2002 | Van Nest et al. |
| 2002/0110569 | A1 | 8/2002 | Granoff et al. |
| 2002/0111323 | A1 | 8/2002 | Martin et al. |
| 2002/0136776 | A1 | 9/2002 | Fang et al. |
| 2002/0137714 | A1 | 9/2002 | Kandimalla et al. |
| 2002/0142974 | A1 | 10/2002 | Kohn et al. |
| 2002/0142977 | A1 | 10/2002 | Raz et al. |
| 2002/0142978 | A1 | 10/2002 | Raz et al. |
| 2002/0156033 | A1 | 10/2002 | Bratzler et al. |
| 2002/0164341 | A1 | 11/2002 | Davis et al. |
| 2002/0165178 | A1 | 11/2002 | Schetter et al. |
| 2002/0183272 | A1 | 12/2002 | Johnston et al. |
| 2002/0197269 | A1 | 12/2002 | Lingnau et al. |
| 2002/0198165 | A1 | 12/2002 | Bratzler et al. |
| 2003/0003579 | A1 | 1/2003 | Kadowaki et al. |
| 2003/0022849 | A1 | 1/2003 | Chang |
| 2003/0022852 | A1 | 1/2003 | Van Nest et al. |
| 2003/0026782 | A1 | 2/2003 | Krieg |
| 2003/0026801 | A1 | 2/2003 | Weiner et al. |
| 2003/0049266 | A1 | 3/2003 | Fearon et al. |
| 2003/0050261 | A1 | 3/2003 | Krieg et al. |
| 2003/0050263 | A1 | 3/2003 | Krieg et al. |
| 2003/0050268 | A1 | 3/2003 | Krieg et al. |
| 2003/0052839 | A1 | 3/2003 | Binley et al. |
| 2003/0055014 | A1 | 3/2003 | Bratzler |
| 2003/0059773 | A1 | 3/2003 | Van Nest et al. |
| 2003/0060440 | A1 | 3/2003 | Klinman et al. |
| 2003/0064064 | A1 | 4/2003 | Dina |
| 2003/0072762 | A1 | 4/2003 | Van de Winkel et al. |
| 2003/0073142 | A1 | 4/2003 | Chen et al. |
| 2003/0078223 | A1 | 4/2003 | Raz et al. |
| 2003/0091599 | A1 | 5/2003 | Davis et al. |
| 2003/0092663 | A1 | 5/2003 | Raz |
| 2003/0096417 | A1 | 5/2003 | Fischer |
| 2003/0100527 | A1 | 5/2003 | Krieg et al. |
| 2003/0104044 | A1 | 6/2003 | Semple et al. |
| 2003/0104523 | A1 | 6/2003 | Bauer et al. |
| 2003/0109469 | A1 | 6/2003 | Carson et al. |
| 2003/0119773 | A1 | 6/2003 | Raz et al. |
| 2003/0119774 | A1 | 6/2003 | Foldvari et al. |
| 2003/0119776 | A1 | 6/2003 | Phillips et al. |
| 2003/0125284 | A1 | 7/2003 | Raz et al. |
| 2003/0129251 | A1 | 7/2003 | Van Nest et al. |
| 2003/0130217 | A1 | 7/2003 | Raz et al. |
| 2003/0133988 | A1 | 7/2003 | Fearon et al. |
| 2003/0135875 | A1 | 7/2003 | Ehrhardt et al. |
| 2003/0138413 | A1 | 7/2003 | Vicari et al. |
| 2003/0138453 | A1 | 7/2003 | O'Hagan et al. |
| 2003/0139364 | A1 | 7/2003 | Krieg et al. |
| 2003/0143213 | A1 | 7/2003 | Raz et al. |
| 2003/0143743 | A1 | 7/2003 | Schuler et al. |
| 2003/0144229 | A1 | 7/2003 | Klinman et al. |
| 2003/0147870 | A1 | 8/2003 | Raz et al. |
| 2003/0148316 | A1 | 8/2003 | Lipford et al. |
| 2003/0148976 | A1 | 8/2003 | Krieg et al. |
| 2003/0148983 | A1 | 8/2003 | Fontoura et al. |
| 2003/0157717 | A1 | 8/2003 | Draghia-Akli |
| 2003/0158136 | A1 | 8/2003 | Rice et al. |
| 2003/0165478 | A1 | 9/2003 | Sokoll |
| 2003/0166001 | A1 | 9/2003 | Lipford |
| 2003/0170273 | A1 | 9/2003 | O'Hagan et al. |
| 2003/0171321 | A1 | 9/2003 | Schmidt et al. |
| 2003/0175731 | A1 | 9/2003 | Fearon et al. |
| 2003/0176373 | A1 | 9/2003 | Raz et al. |
| 2003/0176389 | A1 | 9/2003 | Raz et al. |
| 2003/0180320 | A1 | 9/2003 | Darji et al. |
| 2003/0181406 | A1 | 9/2003 | Schetter et al. |
| 2003/0185848 | A1 | 10/2003 | Johnston et al. |
| 2003/0185900 | A1 | 10/2003 | Choi et al. |
| 2003/0186921 | A1 | 10/2003 | Carson et al. |
| 2003/0191079 | A1 | 10/2003 | Krieg et al. |
| 2003/0199466 | A1 | 10/2003 | Fearon et al. |
| 2003/0203861 | A1 | 10/2003 | Carson et al. |
| 2003/0206967 | A1 | 11/2003 | Choi et al. |
| 2003/0207287 | A1 | 11/2003 | Short |
| 2003/0212026 | A1 | 11/2003 | Krieg et al. |
| 2003/0212028 | A1 | 11/2003 | Raz et al. |
| 2003/0216340 | A1 | 11/2003 | Van Nest et al. |
| 2003/0219752 | A1 | 11/2003 | Short |
| 2003/0220277 | A1 | 11/2003 | Yew et al. |
| 2003/0224010 | A1 | 12/2003 | Davis et al. |
| 2003/0225016 | A1 | 12/2003 | Fearon et al. |
| 2003/0232780 | A1 | 12/2003 | Carson et al. |
| 2004/0005588 | A1 | 1/2004 | Cohen et al. |
| 2004/0006010 | A1 | 1/2004 | Carson et al. |
| 2004/0006032 | A1 | 1/2004 | Lopez |
| 2004/0006034 | A1 | 1/2004 | Raz et al. |
| 2004/0009897 | A1 | 1/2004 | Sokoll |
| 2004/0009942 | A1 | 1/2004 | Van Nest |
| 2004/0009949 | A1 | 1/2004 | Krieg |
| 2004/0013686 | A1 | 1/2004 | Granoff et al. |
| 2004/0013688 | A1 | 1/2004 | Wise et al. |
| 2004/0028693 | A1 | 2/2004 | Wu et al. |
| 2005/0026245 | A1 | 2/2005 | Klinman et al. |

FOREIGN PATENT DOCUMENTS

| | | |
|---|---|---|
| WO | WO 92/21353 | 12/1992 |
| WO | WO 93/17115 | 9/1993 |
| WO | WO 94/19945 | 9/1994 |
| WO | WO 95/05853 | 3/1995 |
| WO | WO 95/18231 | 7/1995 |
| WO | WO 95/26204 | 10/1995 |
| WO | WO 96/02555 | 2/1996 |
| WO | WO 96/24380 | 2/1996 |
| WO | WO 96/35782 | 11/1996 |
| WO | WO 97/28259 | 1/1997 |
| WO | WO 98/29430 | 12/1997 |
| WO | WO 98/11211 | 3/1998 |
| WO | WO 98/14210 | 4/1998 |
| WO | WO 98/16247 | 4/1998 |
| WO | WO 98/18810 | 5/1998 |
| WO | WO 98/32462 | 7/1998 |
| WO | WO 98/37919 | 9/1998 |
| WO | WO 98/40100 | 9/1998 |
| WO | WO 98/49288 | 11/1998 |
| WO | WO 98/49348 | 11/1998 |
| WO | WO 98/52581 | 11/1998 |
| WO | WO 98/55495 | 12/1998 |

| WO | WO 99/11275 | | 3/1999 |
| --- | --- | --- | --- |
| WO | WO 99/27961 | * | 6/1999 |
| WO | WO 99/37151 | | 7/1999 |
| WO | WO 99/51259 | | 10/1999 |
| WO | WO 99/56755 | | 11/1999 |
| WO | WO 99/58118 | | 11/1999 |
| WO | WO 99/61056 | | 12/1999 |
| WO | WO 99/62923 | | 12/1999 |
| WO | WO 00/14217 | | 3/2000 |
| WO | WO 00/20039 | | 4/2000 |
| WO | WO 00/21556 | | 4/2000 |
| WO | WO 00/06588 | | 10/2000 |
| WO | WO 00/61151 | | 10/2000 |
| WO | WO 00/62787 | | 10/2000 |
| WO | WO 00/67023 | | 11/2000 |
| WO | WO 00/67787 | | 11/2000 |
| WO | WO 01/00232 | | 1/2001 |
| WO | WO 01/02007 | | 1/2001 |
| WO | WO 01/12223 | | 2/2001 |
| WO | WO 01/12804 | | 2/2001 |
| WO | WO 01/22990 | | 4/2001 |
| WO | WO 01/51500 | | 7/2001 |
| WO | WO 01/55341 | | 8/2001 |
| WO | WO 01/68077 | | 9/2001 |
| WO | WO 01/68103 | | 9/2001 |
| WO | WO 01/68116 | | 9/2001 |
| WO | WO 01/68117 | | 9/2001 |
| WO | WO 02/11761 A2 | * | 2/2002 |
| WO | WO 02/69369 | | 9/2002 |
| WO | WO 03/054161 | | 7/2003 |

OTHER PUBLICATIONS

Agrawal, "Antisense Oligonucleotides: Toward Clinical Trials". Tibtech 14:376-387 (1996).
Agrawal, "Medicinal Chemistry and Therapeutic Potential of CpG DNA". Trends in Molecular Medicine 8(3):114-121 (2002).
Agrawal, et al., "Absorption, Tissue Distribution and In Vivo Stability in Rats of a Hybrid Antisense Oligonucleotide Following Oral Administration". Biochemical Pharmacology 50(4):571-576 (1995).
Agrawal, et al., "Antisense therapeutics: is it as simple as complementary base recognition?" abstract only, Molecular Med. Today 6(2):72-81 (2000).
Agrawal, et al., "In Vivo Pharmacokinetics of Phosphorothioate Oligonucleotides Containing Contiguous Guanosines". Antisense & Nucleic Acid Drug Development 7:245-249 (1997).
Agrawal, et al., "Pharmacokinetics and Bioavailability of Antisense Oligonucleotides Following Oral and Colorectal Adminstration of Experimental Animals". Handb. Exp. Pharmacol.: Antisense Research and Application 131:525-543 (1998).
Agrawal, et al., "Pharmacokinetics of Antisense Oligonucleotides". Clin. Pharmacokinet 28(1):7 (1995).
Agrawal, et al., "Pharmacokinetics of Oligonucleotides," abstract only, Ciba. Found. Symp. 209:60-78, (1997).
Agrawal, et al., "Pharmacokinetics, biodistribution, and stability of oligodeoxynucleotide phosphorothioates in mice". Proc. Natl. Acad. Sci. USA 88:7595-7599 (1991).
Akhatar et al., "Bacterial DNA evokes epithelial IL-8 production by a MAPK-dependent, NFκB-independent pathway," FASEB Journal, 17:1319-1339, (2003).
Alama, et al., "Antisense Oligonucleotides as Therapeutic Agents". Pharmacol. Res. 36:171-178 (1997).
Amaral, et al., "Leishmania amazonensis: The asian rhesus macaques (Macaca mulatta) as an experimental model for study of cutaneous leishmaniasis". Exp. Parasitol. 82(1):34-44 (1996).
Anderson, "Human Gene Therapy". Nature 392:25-30 (Apr. 1998).
Anderson, et al., "TH2 and 'TH2-like' cells in allergy and asthma; pharmacological perspectives". TiPS 15:324-332 (1994).
Anfossi, et al., "An oligomer complementary to c-myb-encoded mRNA inhibits proliferation of human myeloid leukemia cell lines". Proc. Natl. Acad. Sci. USA 86:3379-3383 (May 1989).
Angier, "Microbe DNA seen as alien by immune system". New York Times p. C1, 2 pages (1995).
Assoian et al., "Cellular transformation by coordinated action of three peptide growth factors from human platelets," Nature, 309:804-806, (1984).

Azad, et al., "Antiviral activity of a phosphorothioate oligonucleotide complementary to RNA of the human cytomegalovirus major immediate-early region". Amtimicrobial Agents and Chemotherapy 37:1945-1954 (1993).
Azuma, "Biochemical and immunological studies on cellular components of tubercle bacilli". Kekkaku 69(9):45-55 (1992).
Azzoni, et al., "Sustained Impairment of IFN-γSecretion in Suppressed HIV-Infected Patients Despite Mature NK Cell Recovery: Evidence for a Defective Reconstruction of Innate Immunity". J. Immunol. 168(11):5764-5770 (2002).
Ballas, et al., "Induction of NK activity in murine and human cells by CpG motifs in oligodeoxynucleotides and bacterial DNA". J. Immunol. 157(5): 1840-1845 (1996).
Banchereau & Steinman, "Dendritic Cells and the Control of Immunity". Nature 392:245-252 (1998).
Banchereau, et al., "Immunobiology of Dendritic Cells". Ann. Rev. Immunol. 18:767-811 (2000).
Barouch, et al., "Control of Viremia and Prevention of Clinical AIDS in Rhesus Monkeys by Cytokine-Augmented DNA Vaccination". Science 290:486-492 (Oct. 2000).
Bauer, et al., "Bacterial CpG-DNA Triggers Activation and Maturation of Human CD11c–, CD123+ Dendritic Cells". J. Immunol. 166:5000-5007 (2001).
Bayever, "Systemic administration of a phosphorothioate oligonucleotide with a sequence complementary to p53 for acute myelogenous leukemia and myelodysplastic syndrome: initial results of a Phase I trial". Antisense Res. Dev. 3:383-390 (1993).
Benimetskaya, et al., "Formation of a G-tetrad and higher order structures correlates with biological activity of the RelA (NF-kBp65) 'antisense' oligodeoxynucleotide". Nucleic Acids Research 25(13):2648-2656 (1997).
Bennett, et al., "DNA binding to human leukocytes: evidence for a recptor-mediated association, internalization, and degradation of DNA". J. Clin. Invest. 76(6):2182-2190 (1985).
Berg, et al., "Interleukin-10 is a central regulator fo the response to LPS in murine models of endotoxic shock and the Shwartzman reaction but not endotoxin tolerance". J. Clin. Invest. 96(5):2339-2347 (1995).
Biolabs, "1988-1989 Catalog, Random Primer #s 1230, 1601, 1602".
Bishop, et al., "Intramolecular G-quartet Motifs Confer Nuclease Resistance to a Potent Anti-HIV Oligonucleotide". The Journal of Biological Chemistry 271(10):5698-5703 (Mar. 1996).
Blanchard, et al., "Interferon-y Induction by Lipopolysaccharide: Dependence of Interleukin 2 and Macrophages". The Journal of Immunology 136(3):963-970 (Feb. 1986).
Blanco, et al., "Induction of Dendritic Cell Differentiation by IFN-α in Systemic Lupus Erythermatosus". Science 294:1540-1543 (2001).
Blaxter, et al., "Genes expressed in Brugia malayi infective third stage larvae". Mol. Biochem. Parasitol. 77:77-93 (1996).
Boggs, et al., "Characterization and modulation of immune stimulation by modified oligonucleotides". Antisense Nucl. Acid Drug Dev. 7(5):461-471 (1997).
Boiarkina, et al., "Dietary supplementals from ground fish meat with DNA for treatment and prophylaxis". Vopr. Pitan 1:29-31 (1998), abstract.
Branda, et al., "Amplification of antibody production by phosphorothioate oligodeoxynucleotides". J. Lab Clin. Med. 128(3):329-338 (1996).
Branda, et al., "Immune stimulation by an antisense oligomer complementary to the rev gene of HIV-1". Biochem. Pharmacol. 45(10):2037-2043 (1993).
Briskin, et al., "Lipopolysaccharide-unresponsive mutant pre-B-cell lines blocked in NF-kappa B activation". Mol. Cell Bio. 10(1):422-425 (1990).
Burgess, "The antiproliferative activity of c-myb and c-myc antisense oligonucleotides in smooth muscle cells is caused by a nonantisense mechanism". Proc. Natl. Acad. Sci. USA 92:4051-4055 (Apr. 1995).
Calarota, et al., "Immune Responses in Asymptomatic HIV-1 Infected Patients After HIV-DNA Immunization Followed by Highly Active Antiretroviral Threatment". J. Immunol. 163(4):2330-2338 (1999).

Chace, et al., "Regulation of differentiation in CD5+ and conventional B cells". Clin. Immunol. Immunopathol. 68(3):327-332 (1993).
Chang, et al., "The palindromic series I repeats in the simian cytomegalovirus major immediate-early promoter behave as both strong basal enhancers and cyclic AMP response elements". J. Virol. 64(1):264-277 (1990).
Chapuis, et al., "Differentiation of Human Dendritic Cells from Monocytes in vitro". Eur. J. Immunol. 27:431-441 (1997).
Chehimi, "Persistent Decreases in Blood Plasmacytoid Dendritic Cell Number and Function Despite Effective Highly Active Antiretroviral Therapy and Increased Blood Myeloid Dendritic Cells in HIV-Infected Individuals". J. Immunol. 168(9):4796-4801 (2002).
Chu, et al., "CpG oligodeoxynucleotides act as adjuvants that switch on T helper 1 (Th1) immunity". J. Exp. Med. 186(10):1623-1631 (1997).
Chun, et al., "Effect of interleukin-2 on the pool of latently infected, resting CD4+ T-cells in HIV-1-infected patients receiving highly active anti-retroviral therapy". Nature Med. 5(6):651-655 (1999).
Chun, et al., "Perspective: Latent reservoirs of HIV: Obstacles to the eradication of virus". Proc. Natl. Acad. Sci. USA 96:10958-10961 (1999).
Clark, "Cutaneous tissue repair: basic biologic considerations," J. Am Acad Dermatol, (Abstract Only), 13:701-725, (1985).
Cohen & Fauci, et al., "HIV/AIDS in 1998—Gaining the Upper Hand?" JAMA 280(1):87-88 (1998).
Cohen, et al., "Exploring How to Get at—and Eradicate—Hidden HIV". Science 279:1854-1855 (1998).
Cook, et al., "Effect of a Single Ethanol Exposure on HIV Replication in Human Lymphocytes". J. Invest. Med. 45(5):265-271 (1997).
Cooper, et al., "Therapeutic Strategies for HIV Infection—Time to Think Hard". The New England Journal of Medicine 339(18):1319-1321 (1998).
Cowdery, et al., "Bacterial DNA induces NKcells to produce IFN-gamma in vivo and increases the toxici of lipopolysaccharides". J. Immunol. 156(12):4570-4575 (1996).
Crosby, et al., "The early responses gene NGF1-C encodes a zinc finger transcriptional activator and is a member of the GCGGGGCG (GSG) element-binding protein family". Mol. Cell Bio. 2:3835-3841 (1991).
Crystal, "Transfer of genes to humans: early lessons and obstacles to success". Science 270:404-410 (1995).
Cryz, et al., "Vaccine Delivery System—European Commission COST/STD Initiative Report of the Expert Panel VII". Vaccine 14(7):665-690 (1996).
D'Andrea, et al., "Interleukin 10 (IL-10) inhibits human lymphocyte interferon gamma-production by suppressing natural killer cell stimulatory factor/IL-12 synthesis in accessory cells". J. Exp. Med. 178(3):1041-1048 (1993).
Davey, et al., "HIV-1 and T-Cell dynamics after interruption of highly antiretroviral therapy (HAART) in patients with a history of sustained viral suppression". Proc. Natl. Acad. Sci. USA 96(26):15109-15114 (1999).
Davis, "Plasmid DNA expression systems for the purpose of immunization". Curr. Opin. Biotechnol. 8(5):635-646 (Oct. 1997).
Davis, et al., "CpG DNA is a Potent Enhancer of Specific Immunity in Mice Immunized with Recombinant Hepatitis B Surface Antigen". J. Immunol. 160(2):870-876 (1998).
Dematos, et al., "Pulsing of Dendritic Cells with Cell Lysates from Either B16 Melanoma or MCA-106 Fibrosarcoma Yields Equally Effective Vaccines Against B16 Tumors in Mice". J. Surg. Oncol. 68:79-91 (1998).
Deml, et al., "Immunostimulatory CpG motifs trigger a T Helper-1 immune response to Human Immunodeficiency Virus Type-1 (HIV-1) gp160 envelope protein". Clin. Chem. Lab. Med. 37(3):199-204 (1999).
Dias et al., "Antisense Oligonucleotides: Basic Concepts and Mechanisms," Mol. Cancer Ther. 1:317-355, 2002.
Doerfler, et al., "On the Insertion of Foreign DNA into Mammalian Genomes: Mechanism and Consequences". Gene 157(1-2):241-254 (1995), abstract.

Durham, et al., "Immunotherapy and Allergic Inflammation". Clin. Exp. Allergy 21 Suppl 1:206-210 (1991).
Eck, et al., "Chapter 5: Gene-Based Therapy". Goodman & Gilman's The Pharmacological Basis of Therapeutics 9th ed.:77-101 (1996).
Elkins, et al., "Bacterial DNA containing CpG motifs stimulates lymphocyte-dependent protection of mice against lethal infection with intracellular bacteria". J. Immunol. 162:2291-2298 (1999).
Englisch, et al., "Chemically modified oligonucleotides as probes and inhibitors". Angew. Chem. Int. Ed. Engl. 30:613-629 (1991).
Erb, et al., "Infection of mice with Mycobacterium bovis-badillus Calmette-Guerin (BCG) supresses allergen-induced airway eosinophilia". J. Exp. Med. 184(4):561-569 (1998).
Etlinger, "Carrier sequence selection—one key to successful vaccines". Immunology Today 13(2):52-55 (1992).
Fanslow, et al., "Effect of Nucleotide Restriction and Supplementation on Resistance to Experimental Murine Candidasis". J. Parenter. Enteral. Nutr. 12(1):49-52 Abstract (1988).
Fields, et al., "Murine Dendritic Cells Pulsed With Whole Tumor Lysates Mediate Potent Antitumor Immune Responses in vitro and in vivo". Proc. Natl. Acad. Sci. USA 95:9482-9487 (1998).
Filion, et al., "Major Limitations in the use of Cationic Liposomes for DNA Delivery". Int. J. Pharmaceuticals 162:159-170 (1998).
Fox, "Mechanism of action of hydroxychloroquine as an antirheumatic drug". Chem. Abstracts 120:15, Abstract No. 182630 (1 page) (1994).
Frantz et al., "Innate Immunity and Angiogenesis," Circulation Research, 96:15-26, (2005).
Freidag, et al., "CpG oligodeoxynucleotides and interleukin-12 improve the efficacy of Mycobacterium bovis BCG vaccination in mice challenged with M. tuberculosis". Infect. Immun. 68:2948-2953 (2000).
Gao, et al., "Phosphorothioate oligonucleotides are inhibitors of human DNA polymerases and Rnase H: Implications for antisense technology". Mol. Pharmacol. 41:223-229 (1992).
Garraud, "Regulation of Immunoglobin Production in Hyper-IgE (Job's) Syndrome". J. Allergy Clin. Immunol. 103(2 Pt 1):333-340 (Feb. 1999).
Gluckman, et al., "In Vitro Generation of Human Dendritic Cells and Cell Therapy". Cytokines Cell Mol. Ther. 3:187-196 (1997).
Gramzinski, et al., "Interleukin-12- and gamma interferon-dependent protection against malaria conferred by CpG oligodeoxynucleotide in mice". Infect. Immun. 69(3):1643-1649 (2001).
Gura, "Antisense has growing pains". Science 270:575-576 (1995).
Gursel, "Sterically Stabilized Cationic Liposomes Improve the Uptakeand Immunostimulatory Activity of CpG Oligonucleotides". J. Immunol. 167(6):3324-3328 (2001).
Gursel, et al., "Differential and Competitive Activation of Human Immune Cells by Distinct Classes of CpG Oligodeoxynucleotide". J. Leuko. Biol. 71:813-820 (2002).
Hadden, et al., "Immunopharmacology". JAMA 268(20):2964-2969 (1992).
Hadden, et al., "Immunostimulants". TiPS 141:169-174 (1993).
Halpern, et al., "Bacterial DNA induces murine interferon-gamma production by stimulation of interleukin-12 and tumor necrosis factor-alpha". Cell Immunol. 167(1):72-78 (1996).
Haslett, et al., "Strong Human Immunodificiency Virus (HIV) Specific CD4+ T Cell Responses in a Cohort of Chronically Infected Patients are Associated with Interruptions in Anti-HIV Chemotherapy". J. Infect. Diseases 181:1264-1272 (2000).
Hatzfeld, "Release of early human hematopoietic progenitors from quiescence by antisense transformin owth factor β1 or Rb oligonucleotides". J. Exp. Med. 174:925-929 (1991).
Havlir, et al., "Maintenance Antiretroviral Therapies in HIV-Infected Subjects with Undetectable Plasma HIV RNA after Triple-Drug Therapy". The New England Journal of Medicine 339(18):1261-1268 (1998).
Hayashi, et al., "Enhancement of innate immunity against Mycobacterium avium infection by immunostimulatory DNA is mediated by indoteamine 2,3-dioxygenase". Infect. Immun. 69:6156-6164 (2001).
Hertl, et al., "Inhibition of Interferon-y-Induced Intercellular Adhesion Molecule-1 Expression on Human Keratinocytes by Phosphorothioate Antisense Oligodeoxynucleotides is the Consequence of Antisense-Specific and Antisense-Non-Specific Effects". The Journal of Investigative Dermatology 104(5):813-818 (May 1995).
Highfield, "Sepsis: the more, the murkier". Biotechnology 12:828 (1994).
Hoeffler, et al., "Identification of multiple nuclear factors that interact with cyclic adenosine 3',5'-monophosphate response element-binding protein and activating transcription factor-2 by protein-protein interactions". Mol. Endocrinol. 5(2):256-266 (1991).
Honess et al., *J. Gen Vir.* 70(4):837-855, (1989).
Honess, et al., "Deviations from Expected Frequencies of CpG Dinucleotides in Herpesvirus DNAs May be Diagnostic of Differences in the States of Their Latent Genomes". J. Gen. Vir. 70(4):837-855 (1989).
Horspool, et al., "Nucleic acid vaccine-induces immune responses require CD28 costimulation and are regulated by CTLA4". J. Immunol. 160:2706-2714 (1998).
Hughes, et al., "Influence of Base Composition on Membrane Binding and Cellular Uptake of 10-mer Phosphorothioate Oligonucleotides in Chinese Hamster Ovary (CHRC5) Cells". Antisense Research and Development 4:211-215 (1994).
Iguchi-Ariga, et al., "CpG methylation of the cAMP-responsive enhancer/promoter sequence TGACGTCA abolishes specific factor binding as well as transcriptional activation". Genes Dev. 3(5):612-619 (1989).
Imami, et al., "Assessment of Type 1 and Type 2 Cytokines in HIV Type 1-Infected Individuals: Impact of Highly Active Antiretroviral Therapy". AIDS Research and Human Retroviruses 15(17):1499-1508 (1999).
Inoue and Aramaki, "Toll-like receptor-9 expression induced by tape-stripping triggers on effective immune response with CpG-oligodeoxynuleotides," (Abstract Only), Vaccine, 6:1007-1013, (Jan. 22, 2007).
Ishibashi et al., *Cancer Research* 60:6531-6536, (2000).
Ishibashi, et al., "Sp1 Decoy Transfected to Carcinoma Cells Suppresses the Expression of Vascular Endothelial Growth Factor, Transforming Growth Factor β, and Tissue Factor and Also Cell Growth and Invasion Activities". Cancer Research 60:6531-6536 (2000).
Ishikawa, et al., "IFN induction and associated changes in splenic leukocyte distribution". J. Immunol. 150(9):3713-3727 (1993).
Iversen, et al., "Pharmacokinetics of an antisense phosphorothioate oigodeoxynucleotide against rev from human immunodeficiency virus type 1 in the adult male rat following single inections and continuous infusion". Antisense Res. Dev. 4:43-52 (1994).
Jakway, et al., "Growth regulation of the B lymphoma cell line WEHI-23 1 by anti-immunoglobulin, lipopolysaccharide, and other bacterial products". J. Immunol. 137(7):2225-2231 (1996).
Jaroszewski, et al., "Cellular uptake of antisense oligonucleotides". Adv. Drug Delivery Rev. 6(3):235-250 (1991).
Jilek, et al., "Antigen-Independent Suppression of the Allergic Immune Response to Bee Venom Phospholipase A2 by DNA Vaccination in CBA/J Mice". J. Immunol. 166:3612-3621 (2001).
Jones, et al., "Synthetic Oligonucleotides Containing CpG Motifs Enhance Immunogenicity of a Peptide Malaria Vaccine in Aotus Monkeys". Vaccine 17:3065-3071 (1999).
Juffermans, et al., "CpG oligodeoxynucleotides enhance host defense during murine tuberculosis". Infect. Immun. 70:147-152 (2002).
Kadowaki, et al., "Distinct CpG DNA and Polyinosinic-Polycytidylic Acid Double Stranded RNA, Respectively, Stimulate CD11c- Type 2 Dendritic Cell Precursoes and CD11c+ Dendritic cells to Produce Type I IFN". J. Immunol. 166:2291-2295 (2001).
Kataoka, et al., "Antitumor activity of synthetic oligonucleotides with sequences from cDNA encodin proteins of *Mycobacterium bovis* BCG". Jpn. J. Cancer Res. 83:244-247 (1992).
Kenney, et al., "Protective Immunity Using Recombinant Human IL-12 and Alum as Adjuvants in a Primate Model of Cutaneous Leishmaniasis". J. Immunol. 163(8):4481-4488 (1999).
Khaled, et al., "Multiple mechanisms may contribute to the cellular anti-adhesive effects of phosphorothioate oligodeoxynucleotides". Nucleic Acids Research 24(4):737-745 (1996).

Kimura, et al., "Binding of oligoguanylate to scavenger receptors is required for oligonucleotides to augment NK cell activity and induce IFN". J. Biochem 116(5):991-994 (1994).
Kitagaki et al., "Oral administration of CpG-ODNs suppresses antigen-induced asthma in mice," *Clinical and Experimental Immunology*, 143:249-259, (2005).
Kline, et al., "CpG motif oligonucleotides are effective in prevention of eosinophilic inflammation in a murine model of asthma". *J. Invest. Med.*, 44(7):380A, (1 page) (1996).
Kline, et al., "CpG oligonucleotides can reverse as well as prevent TH2-mediated inflammation in a murine model of asthma". J. Invest. Med. 45(7):298A, (1 page) (1997).
Kline, et al., "Immune redirection by CpG oligonucleotides, Conversion of a Th2 response to a Th 1 response in a murine model of asthma". J. Invest. Med. 45(3):282A (1 page) (1997).
Klinman et al., "Activation of the innate immune system by CpG oligodeoxynucleotides: immunoprotective activity and safety". Springer Semin. Immunopathol. 22:173-183 (2000).
Klinman et al., "CpG Motids as Immune Adjuvants". Vaccine 17:19-25 (1999).
Klinman et al., "CpG motifs present in bacteria DNA rapidly induce lymphocytes to secrete interleukin 6, interleukin 12, and interferon gamma". Proc. Natl. Acad. Sci. USA 93(7):2879-2883 (1996).
Klinman et al., "Immune recognition of foreign DNA: a cure for bioterrorism?" Immunity 11:123 (1 page) (1999).
Klinman et al., "Immunotherapeutic Use of CpG Oligodeoxynuvcleotides," *Immunology*, 4:1-10, (Apr. 2004).
Klinman, et al., "Repeated administration of synthetic oligodeoxynuctetides expressing CpG motifs provides tong-term protection against bacterial infection". Infect. Immun. 67:5658-5663 (1999).
Kou, et al., "Analysis and Regulation of interferon-gamma production by peripheral blood lymphocytes from patients with bronchial asthma". Arerugi 43(3):483-491 (1994), abstract.
Krieg, "An innate immune defense mechanism based on the recognition of CpG motifs in microbial DNA". J. Lab. Clin. Med. 128(2):128-133 (Abstract) (1996).
Krieg, et al., "A role for endogenous retroviral sequences in the regulation of lymphocyte activation". J. Immunol. 143(8):2448-2451 (1989).
Krieg, et al., "Brief Communication: Oligodeoxynucleotide Modifications Determine the Magnitude of B-Cell Stimulation by CpG Motifs". Antisense & Nucleic Acid Drug Development 6:133-139 (1996).
Krieg, et al., "Causing a Commotion in the Blood: Immunotherapy Progresses from Bacteria to Bacterial DNA". Immunology Today 21(10):521-526 (2000).
Krieg, et al., "CpG DNA induces sustained IL-12 expression in vivo and resistance to *Listeria* monocytogenes challenge". J. Immunol. 161:2428-2434 (1998).
Krieg, et al., "CpG DNA: A pathogenic factor in systemic lupus erythematosus?". J. Clin. Immunol. 15(6):284-292 (1995).
Krieg, et al., "CpG motifs in bacterial DNA and their immune effect". Annu. Rev. Immunol. 20:709-760 (2002).
Krieg, et al., "CpG motifs in bacterial DNA trigger direct B-cell activation". Nature 374:546-549 (1995).
Krieg, et al., "Leukocyte stimulation by oligodeoxynucleotides". Applied Antisense Oligonucleotide Tech. (BOOK):431-448 (1998).
Krieg, et al., "Modification of antisense phosphodiester oligodeoxynucleotides by a 5' cholesteryl moiety increases cellular association and improves efficacy". Proc. Natl. Acad. Sci. USA 90:1048-1052 (1993).
Krieg, et al., "Phosphorothioate oligodeoxynucleotides: antisense or anti-protein?" Antisense Res. Dev. 5:241 (1 page) (1995).
Krieg, et al., "The role of CpG dinucleotides in DNA vaccines". Trends in Microbiol. 6:23-27 (1998).
Krieg, et al., "Uptake of oligodeoxyribonucleotides by lymphoid cells is heterogeneous and inducible". Antisense Res. Dev. 1(2):161-171 (1991).
Krieger, et al., "Structures and Functions of Multiligand Lipoprotein Receptors: Macrophage Scavenger Receptors and LDL Receptor-Related Protein (LRP)" Annu. Rev. Biochem 63:601-637 (1994).

Krug, et al., "Identification of CpG Oligonucleotide Sequences with High Induction of IFN-α/βin Plasmacytoid Dendritic Cells," Eur. J. Immunol. 31:2154-2163 (2001).

Krug, et al., "Toll-like Receptor Expression Reveals CpG DNA as a Unigue Microbial Stimulus for Plasmacytoid Dendritic Cells Which Synergizes With CD40 Ligand to Induce High Amounts of IL-12," Eur. J. Immunol. 31:3026-3037 (2001).

Kuchan, et al., "Nucleotides in Infant Nutrition: Effects of Immune Function," Pediatr. Adolesc. Med. Basel. Karger 8:80-94 (1998).

Kulkarni, et al., "Effect of Dietary Nucleotides on Response to Bacterial Infection," J. Parenter. Enteral. Nutr. 10(2):169-171 Abstract (1986).

Kuramoto, et al., "Oligonucleotide sequences required for natural killer cell activation," Jpn. J. Cancer Res. 83:1128-1131 (1992).

Lagrange, et al., "Immune Responses Directed Against Infectious and Parasitic Agents," Immunology (BOOK—ISBN:0471017604) (Chapter of Book; Ed-Jean-François Bach): (1978).

Lang, et al., "Guanosine-rich oligodeoxynucleotides induce proliferation of macrophage progenitors in cultures of murine bone marrow cells," Eur. J. Immunol. 29:3496-3506 (1999).

Lapatschek, et al., "Activation of Macrophages and B Lymphocytes by an Oligodeoxynucleotide Derived from an Acutely Pathogenic Simian Immunodeficiency Virus," Antisense Nucleic Acid Drug Dev. 8(5):357-370 (Oct. 1998).

Ledergerber, et al., "Clinical Progression and Virological Failure on Highly Active Antiretroviral Therapy in HIV-1 Patients: a Prospective Cohort Study," The Lancet 353:863-868 (1999).

Lederman, et al., "Polydeooxyguanine Motifs in a 12-mer Phosphorothioate Oligodeooxynucleotide Augment Binding to the v3 Loop of the HIV-1 gp120 and Potency of HIV-1 Inhibition Independently of G-Tetrad Formation," Antisense & Nucleic Acid Drug Development 6:281-289 (1996).

Lee, et al., "An Oligonucleotide Blocks Interferon-y Signal Transduction," Transplantation 62(9):1297-1301 (1996).

Leibson, et al., "Role of γ-interferon in antibody-producing responses," Nature 309:799-801 (1984).

Leonard, et al., "Conformation of guanine 8-oxoadenine base pairs in the crystal structure of d(CGCGAATT(O8A)GCG)," Biochemistry 31(36):8415-8420 (1992).

Li et al., "CpG DNA-mediated immune response in pulmonary endothelial cells," *Am J Physiol Lung Cell Mol Physiol*, 287:L552-L558, (2004).

Li, et al., "Long-Lasting Recovery in CDR T-Cell Function and Viral-Load Reduction After Highly Active Antiretroviral Therapy in Advanced HIV-1 Disease," The Lancet 351:1682-1686 (1998).

Liang, et al., "Activation of Human B Cells by Phosphorothioate Oligodeoxynucleotides," *J. Clin. Invest.*, 98:1119-1129, (1996).

Lipford, et al., "CpG-containing synthetic oligonucleotides promote B and cytotoxic T cell responses to protein antigen: a new class of vaccine adjuvants," Eur. J. Immunol. 27(9):2340-2344 (1997).

Lipford, et al., "Immunostimulatory DNA: sequence-dependent production of potentially harmful or useful cytokines," Eur. J. Immunol. 27(12):3420-3426 (1997).

Lönnberg, et al., "Towards Genomic Drug Therapy with Antisense Oligonucleotides,". Ann. Med. 28:511-522 (1996).

Macaya, et al., "Thrombin-binding DNA aptamer forms a unimolecular quadruplex structure in solution," Proc. Natl. Acad. Sci. USA 90:3745-3749 (Apr. 1993).

MacFarlane, et al., "Antagonism of immunostimulatory CpG-oligodeoxynucleotides by quinacrine, chloroquine, and structurally related compounds," J. Immunol. 160(3):1122-1131 (1998).

Maddon, "The Isolation and Nucleotide Sequence of a cDNA Encoding the T Cell Surface Protein T4: A New Member of the Immunoglobin Gene Family," Cell 42(1):93-104 (1985).

Maltese, et al., "Sequence context of antisense RelA/NF-kB phohphorothioates determines specificity," Nucleic Acids Research 23(7):1146-1151 (1995).

Manzel, et al., "Lack of Immune Stimulation by Immobilized CpG-oligonucletide," Antisense & Nucleic Acid Drug Development 9(5):459-464 (1999).

Martin-Armas et al., "Toll-like receptor 9 (TLR9) is present in murine liver sinusoidal endothelial cells (LSECs) and mediates the effect of CpG-oligonucleotides," Journal of Hepatology, 44:939-946, (2006).

Mastrangelo, et al., "Gene therapy for human cancer: an essay for clinicians," Seminars Oncology 23(1):4-21 (1996).

Matson, et al., "Nonspecific suppression of [3H]thymidine incorporation by control oligonucleotides," Antisense Res. Dev. 2(4):325-330 (1992).

McCluskie, et al., "Cutting Edge: CpG DNA Is a Potent Enhancer of Systemic and Mucosal Immune Responses Against Hepatitis B Surface Antigen with Intranasal Administration to Mice," J. Immun. 161:4463-4465 (1998).

McCluskie, et al., "Route and Method of DNA Vaccine Influence Immune Responses in Mice and Non-Human Primates," Molecular Med. 5(5):287-300 (1999).

McIntyre, et al., "A sense phosphorothioate oligonucleotide directed to the initiation codon of transcription factor NF-kappa B p65 causes sequence-specific immune stimulation," Antisense Res. Dev. 3(4):309-322 (1993).

McKenzie, "Nucleic Acid Vaccines," Immunologic Res. 24(3):225-244 (2001).

Merad, et al., "In vivo Manipulation of Dendritic Cells to Induce Therapeutic Immunity," Blood 99(5):1676-1682 (2002).

Messina, et al., "Stimulation of in vitro murine lymphocyte proliferation by bacterial DNA," Cell Immunol. 147(6):1759-1764 (1991).

Messina, et al., "The influence of DNA structure on the in vitro stimulation of murine lymphocytes by natural and synthetic polynucleotide antigens," J. Immunol. 147:148-157 (1993).

Mirmohammadsadegh, et al., "Reaction of Keratinocytes to Exogenous DNA," *Cells Tissues Organs*, 172:86-95, (2002).

Mojcik, et al., "Administration of a phosphorothioate oligonucleotide antisense murine endogenous retroviral MCF env causes immune effect in vivo in a sequence-specific manner," Clin. Immunol. Immunopathol. 67(2):130-136 (1993).

Moss & Lederman, "Immunication of the Immunocompromised Host," Clinical Focus on Primary Immune Deficiencies 1(1):1-3 (1998).

Mottram, et al., "A novel CDC2-related protein kinase from *Leishmania mexicana*, LmmCRK1, is post-translationally regulated during the life cycle," J. Biol. Chem. 268(28):21044-21052 (1993).

Nyce, et al., "DNA antisense therapy for asthma in an animal model," Nature 385:721-725 (1997).

Oberbauer, "Not nonsense but antisense—Applications of Antisense Oligonucleotides in Different Fields of Medicine," Wein Klin Wochenschr 109:40-46 (1997).

Ogg, et al., "Quantitation of HIV-1-Specific Cytotoxic T-Lymphocytes and Plasma Load of Viral RNA," Science 279:2103-2106 (1998).

Okada, et al., "Bone Marrow-Derived Dendritic Cells Pulsed With a Tumor-Specific Peptide Elicit Effective Anti-Tumor Immunity Against Intracranial Neoplasms," Int. J. Cancer 78:196-201 (1998).

Palucka, et al., "Dendritic Cells as the Terminal Stage of Monocyte Differentiation," J. Immunol. 160:4587-4595 (1999).

Papasavvas, et al., "Enhancement of Human Immunodeficiency Virus Type I-Specific CD4 and CD8 T Cell Responses in Chronically Infected Persons after Temporary Treatement Interruption," J. Infect. Diseases 182:766-775 (2000).

Pialoux, et al., "A Randomized Trial of Three Maintenance Regimens Given After Three Months of Induction Therapy with Zidovudine, Lamivudine, and Indinavie in Previously Untreated HIV-1-Infected Patients," The New England Journal of Medicine 339(18):1269-1276 (1998).

Piscitelli, "Immune-Based Therapies for Treatment of HIV Infection," The Annals of Pharmacotherapy 30:62-76 (1996).

Pisetsky, "Immunological consequences of nucleic acid therapy," Antisense Res. Dev. 5:219-225 (1995).

Pisetsky, "Stimulation of in vitro proliferation of murine lymphocytes by synthetic oligodeoxyucleotides," Molecular Biol. Reports 18:217-221 (1993).

Pisetsky, "The immunological properties of DNA," J. Immunol. 156:421-423 (1996).

Pisetsky, et al., "Immunological Properties of Bacterial DNA," Ann. NY Acad. Sci. 772:152-163 (1995).
Pisetsky, et al., "Stimulation of murine lymphocyte proliferation by a phosphorothioate oligonucleotide with antisense activity for hepes simplex virus," Life Science 54:101-107 (1994).
Platz et al., "Microbial DNA Induces a Host Defense Reaction of Human Respiratory Epithelial Cells," Journal of Immunology, 173:1219-1223, (2004).
Plenat, "Animal models of antisense oligonucleotides: lessons for use in humans," J. Mol. Med. Today 2(6):250-257 (1996).
Prasad, et al., "Oligonucleotides Tethered to a Short Polyguanylic Acid Stretch are Targeted to Macrophages: Enhanced Antiviral Activity of a Vesicular Stomatitis Virus-Specific Antisense Oligonucleotide," Antimicrobial Agents and Chemotherapy 43(11):2689-2696 (Nov. 1999).
Quddus, et al., "Treating activated CD4+ T cells with either of two distinct DNA methyltransferase inhibitors, 5-azacytidine or procaniamide, is sufficient to cause a lupus-like disease in syngeneic mice," J. Clin. Invest. 92(1):38-53 (1993).
Ramanathan, et al., "Characterization of the Oligodeoxynucleotide-mediated Inhibition of Interferon-y-induced Major Histocompatibility Complex Class I and Intercellular Adhesion Molecule-1," The Journal of Biological Chemistry 269(40):24564-24574 (Oct. 1994).
Ramanathan, et al., "Inhibition of Interferon-y-Induced Major Histocompatibility Complex Class I Expression by Certain Oligodeoxynucleotides," Transplantation 57(4):612-615 (Feb. 1994).
Raz, "Deviation of the Allergic IgE to an IgG Response by Gene Immunotherapy," Int. Rev. Immunol. 18(3):271-289 (1999).
Raz, et al., "Intradermal gene immunization: the possible role of DNA uptake in the induction of cellular immunity to viruses," Proc. Natl. Acad. Sci. USA 91:9519-9523 (1994).
Raz, et al., "Preferential Induction of a Th1 Immune Response and Inhibition of Specific IgE Antibody Formation by Plasmid DNA Immunization," Proc. Natl. Acad. Sci. USA 93:5141-5145 (1996).
Ricci, et al., "T cells, cytokines, IgE and allergic airways inflammation," J. Invest. Allergol Clin. Immunol. 4(5):214-220 (1994).
Rojanasakul, "Antisense oligonucleotide therapeutics: drug delivery and targeting," Drug Delivery Reviews 18:115-131 (1996).
Roman, et al., "Immunostimulatory DNA sequences function as T helper-l-promoting aduvants," Nature Med. 3(8):849-854 (1997).
Rosenberg, et al., "Immune Control of HIV-1 After Early Treatment of Acute Infection," Nature 407:523-526 (2000).
Rosenberg, et al., "Vigorous HIV-1-Specific CD4+ T-Cell Responses Associated with Control of Viremia," Science 278:1447-1450 (1997).
Ruiz, et al., "Structured Treatment Interruption in Chronically HIV-1 Infected Patients After Long-Term Viral Suppression," AIDS 14:397-403 (2000).
Santini, et al., "Type I Interferon as a Powerful Adjuvant for Monocyte-derived Dendritic Cell Development and Activity In Vitro and in Hu-PBL-SCID Mice," J. Exp. Med. 191:1777-1788 (2000).
Sato, et al., "Immunostimulatory DNA sequences necessary for effective intradermal gene immunization," Science 273:352-354 (1996).
Scanlon, et al., "Oligonucleotide-mediated Modulation of Mammalian Gene Expression," FASEB J. 9:1288-1295 (1995).
Schnell, et al., "Identification and characterization of a *Saccharomyces cerevisiae* gene (PAR 1) conferring resistance to iron chelators," Eur. J. Biochem. 200:487-493 (1991).
Schoofs, "Small Steps—A Limited Experiment Opens New Approach in Fight Against HIV," Wall Street Journal (Sep. 28, 2000).
Schubert, et al., "Ingested Foreign (phage M13) DNA Survives Transiently in the Gastrointestinal Tract and Enters the Bloodstream of Mice," Mol. Gen. Genet. 242:495-504 (1994).
Schwartz, et al., "CpG motifs in bacterial DNA cause inflammation in the lower respiratory tract," J. Clin. Invest. 100(1):68-73 (1997).
Schwartz, et al., "Endotoxin responsiveness and grain dust-induced inflammation in the lower respiratory tract," Am. J. Physiol. 267(5):609-617 (1994).
Schwartz, et al., "The role of endotoxin in grain dust-induced lung disease," Am. J. Respir. Crit. Care Med. 152(2):603-608 (1995).
Sedegah, et al., "Intertukin 12 induction of interferon g-dependent protection against malaria," Proc. Natl. Acad. Sci. USA 91:10700-10792 (1994).
Sethi, et al., "Postexposure prophytaxis against prion disease with a stimulator of innate immunity," Lancet 360:229-230 (2002).
Shafer, et al., "Highly Active Antiretroviral Therapy (HAART) for the Treatment of Infection With Human Immunodeficiency Virus Type 1," Biomed. & Pharmachther. 53:73-86 (1999).
Shirakawa, et al., "The inverse association between tuberculin responses and atopic disorder," Science 275(5296):77-79 (1997).
Sidman, et al., "γ-Interferon is one of several direct B cell-maturing lymphokines," Nature 309:801-804 (1984).
Sparwasser, et al., "Bacterial DNA and immunostimulatory CpG oligonuceotides trigger maturation and activation of murine dendritic cells," Eur. J. Immunol. 28:2045-2054 (1998).
Sparwasser, et al., "Macrophages sense pathogens via DNA motifs: induction of tumor necrosis factor-alpha-mediated shock," Eur. J. Immunol. 27(7):1671-1679 (1997).
Spiegelberg, et al., "Recognition of T Cell Epitopes and Lymphokine Secretion by Rye Grass Allergen Lolium perenne I-Specific Human T Cell Clones," J. of Immunology 152:4706-4711 (1994).
Stacey, et al., "Immunostimulatory DNA as an adjuvant in vaccination against *Leishmania major*," Infect. Immun. 67:3719-3726 (1999).
Stein, et al., "Oligodeoxynucleotides as inhibitors of gene expression: a review". Cancer Res. 48:2659-2668 (1998).
Stull, et al., "Antigene, ribozyme, and aptamer nucleic acid drugs: progress and prospects," Pharm. Res. 12(4):465-483 (1995).
Su, et al., "Vaccination against Chlamydial Genital Tract Infection after Immunization with Dendritic Cells Pulsed Ex Vivo with Nonviable Chlamydiae," J. Exp. Med. 188:809-818 (1998).
Subramanian, et al., "Theoretical considerations on the 'spine of hydration' in the minor groove of d(CGCGAATTCGCG) d(CGGCT-TAAGCGC): Monte Carlo computer simulation," Proc. Natl. Acad. Sci. USA 85:1836-1840 (1988).
Syme, et al., "Generation of Dendritic Cells ex vivo: Differences in Steady State versus Mobilized Blood from Patients with Breast Cancer, with Lymphoma, and from Normal Donors," J. Hematother. Stem Cell Res. 10:621-630 (2001).
Tanaka, et al., "An antisense oligonucleotide complementary to a sequence in I gamma 2b increases gamma 2b germhine transcripts, stimulates B cell DNA synthesis and inhibits immunoglobulin secretion," J. Exp. Med. 175:597-607 (1992).
Tarte, et al., "Extensive characterization of dendritic cells generated in serum-free conditions: regulation of soluble antigen uptake, apoptotic tumor cell phagocytosis, chemotaxis and T cell activation during maturation in vitro," Leukemia 14:2182-2192 (2000).
Thorne, "Experimental grain dust atmospheres generated by wet and dry aerosolization techniques," Am. J. Ind. Med. 25(1):109-112 (1994).
Tighe, et al., "Conjunction of Protein to Immunostimulatory DNA results in a Rapid Long-Lasting and Potent Induction of Cell-Mediated and Humoral Immunity," Eur. J. Immunol. 30:1939-1947 (2000).
Tokunaga, et al., "A synthetic single-stranded DNA, poly(dG, dC), induces interferon-α/β and -γ, augments natural killer activity and suppresses tumor growth," Jpn. J. Cancer Res. 79:682-686 (1988).
Tokunaga, et al., "Synthetic oligonucleotides with particular base sequences from the cDNA encoding proteins of *Mycobacterium bovis* BCG induce interferons and activate natural killer cells," Microbiol. Immunol. 36(1):55-66 (1992).
Uhlmann, et al., "Antisense oligonucleotides: a new therapeutic principle," Chem. Rev. 90:543-584 (1990).
Verdijk, et al., "Polyriboinosinic Polyribocytidylic Acid (Poly(I:C)) Induces Stable Maturation of Functionally Active Human Dendritic Cells," J. Immunol. 163:57-61 (1999).
Verma, et al., "Gene therapy—promises, problems and prospects," Nature 389:239-242 (Sep. 1997).
Verthelyi, et al., "CpG Oligodeoxynucleotides as Vaccine Adjuvants in Primates," J. Immunol. 168:1659-1663 (2002).
Verthelyi, et al., "Human Peripheral Blood Cells Differentially Recognize and Respond to Two Distinct CpG Motifs," J. Immunol. 166:2372-2377 (2001).

Vil'ner, "Effect of Amphotericin B on the interferonogenic activity of poly(G).poly (C) and poly(G,I).poly(C) in mice and their resistance to infection by the tick-borne encephalitis virus," Antibiotiki 27(11):827-830 (Nov. 1982), abstract.

Vil'ner, "Effect of the size of the continuous poly(G) site in poly(G,A).poly(C) complexes on their interferon-inducing activity and their capacity to stimulate the development of the immunity," Vopr Virusol 31(6):697-700 (1986), abstract.

Vil'ner, et al., "Dependence of the antiviral activity of the poly(G).poly(C) complex on the size of the continuous poly(C) segments," Vopr Virusol 33(3):331-335 (1988), abstract.

Vil'ner, et al., "Effect of virazole on the antiviral activity of poly(G) X poly © and other polyribonucleotide interferongens," Antibiotiki 29(6):450-453 (1984), abstract.

Vil'ner, et al., "Evaluation of the size of the continuous poly(G) site necessary for the biological activity of the poly(G).poly(C) complex," Vopr Virusol30(3):337-340 (1985), abstract.

Wagner, "Bacterial CpG DNA Activates Immune Cells to Signal Infectious Danger". Adv. Immunol. 73:329-368 (1999).

Wagner, "Gene inhibition using antisense oligodeoxynucleotides," Nature 372:333-335 (1994).

Walker, et al., "Activated T Cells and Cytokines in Bronchoalveolar Lavages from Patients with Various Lung Diseases Associated with *Eosinophilia*," Am. J. Respir. Crit. Care Med. 150:1038-1048 (1994).

Walker, et al., "Immunostimulatory oligodeoxynucleotides promote protective immunity and provide systemic therapy for leishmaniasis via IL-12- and IFN-g-dependent mechanisms," Proc. Natl. Acad. Sci. USA 96:6970-6975 (1999).

Wallace, et al., "Oligonucleotide probes for the screening of recombinant DNA libraries," Methods Enzymol. 152:432-442 (1987).

Watson and McKay "The immunophysiological impact of bacterial CpG DNA on the gut," Clinica Chimica Acta, 364:1-11, (2006).

Weiner, "The immunobiology and clinical potential of immunostimulatory CpG oligodeoxynucleotides," Leukocyte Bio. 68:455-463 (2000).

Weiner, et al., "Immunostimulatory oligodeoxynucleotides containing the CpG motif are effective as immune adjuvants in tumor antigen immunization," Proc. Natl. Acad. Sci. USA 94:10833-10837 (1997).

Weiss, "Upping the antisense ante: scientists bet on profits from reverse genetics," Science 139:108-109 (1991).

Whalen, "DNA vaccines for emerging infection diseases: what if?,". Emerg. Infect. Dis. 2(3):168-175 (1996).

Whalen, et al., "DNA-Mediated Immunization to the Helatitis B Surface Antigen: Activation and Entrainment of the Immune Response," Ann. NY Acad. Sci. 772:64-76 (1995).

Wloch, et al., "The influence of DNA sequence on the immunostimulatory properties of plasmid DNA vectors," Hum. Gene Ther. 9(10):1439-1447 (Jul. 1998).

Woolridge, et al., "Immunostimulatory oligodeoxynucleotides containing CpG motifs enhance the efficacy of monoclonal antibody therapy of lymphoma," Blood 89:2994-2998 (1997).

Wu, et al., "Receptor-mediated gene delivery and expression in vivo," J. Biol. Chem. 263:14621-14624 (1988).

Wu-Pong, "Oligonucleotides: opportunities for drug therapy and research," Pharmaceutical Tech. 18:102-114 (1994).

Wyatt, et al., "Combinatorially selected guanosine-quartet structure is a potent inhibitor of human immundeficiency virus envelope-mediated cell fusion," Proc. Natl. Acad. Sci. USA 91:1356-1360 (Feb. 1994).

Yamamoto, "Unique palindromic sequences in synthetic oligonucleotides are required to induce inf and augment INF-mediated natural killer activity," J. Immunol. 148(12):4072-4076 (1992).

Yamamoto, et al., "Ability of oligonucleotides with certain palindromes to induce interferon production and augment natural killer cell activity is associated with their base length," Antisense Res. Dev. 4:119-123 (1994).

Yamamoto, et al., "DNA from bacteria, but not vetebrates, induces interferons, activates natural killer cells, and inhibits tumor growth," Microbiol. Immunol. 36(9):983-997 (1992).

Yamamoto, et al., "In vitro augmentation of natural killer cell activity and production of interferon-alpha/beta and -gamma with deoxyribonucleic acid fraction from *Mycobacterium bovis* BCG," Jpn. J. Cancer Res. 79:866-873 (1988).

Yamamoto, et al., "Lipofection of synthetic oligodeoxyribonucleotide having a palindromic sequence AACGTT to murine splenocytes enhances interferon production and natural killer activity," Microbiol. Immunol. 38(10):831-836 (1994).

Yamamoto, et al., "Mode of action of oligonucleotide fraction extracted from *Mycobacterium bovis* BeG," Kekkaku 69(9):29-32 (1994).

Yamamoto, et al., "Synthetic oligonucleotides with certain palindromes stimulate interferon production of human peripheral blood lymphocytes in vitro," Jpn. J. Cancer Res. 85:775-779 (1994).

Yaswen, et al., "Effects of Sequence of Thioated Oligonucleotides on Cultured Human Mammary Epithelial Cells," Antisense Research and Development 3:67-77 (1993).

Yew, et al., "Contribution of Plasmid DNA to Inflammation in the Lung After Administration of Cationic Lipid: pDNA Complexes," Hum. Gene Ther. 10(2):223-234 (1999).

Yi, et al., "IFN-γ promotes IL-6 and lgM secretion in response to CpG motifs in bacterial DNA and oligonucleotides," J. Immunol. 156:558-564 (1996).

Yi, et al., "Rapid immune activation by CpG motifs in bacterial DNA," J. Immunol. 157:5394-5402 (1996).

Zelphati, et al., "Inhibition of HIV-1 Replication in Cultured Cells with Antisense Oligonucleotides Encapsulated in Immunoliposomes," Antisense Res. Dev. 3:323 (1993).

Zhang, et al., "Antigen- and Isotype-Specific Immune Responses to a Recombinant Antigen-Allergen Chimeric (RAAC) Protein," J. Immunol. 151:791-799 (1993).

Zhao, et al., "Comparison of cellular binding and uptake of antisense phosphodiester, phosphorothioate, and mixed phosphorothioate and methylphosphonate oligonucleotides," Antisense Res. Dev. 3(1):53-66 (1993).

Zhao, et al., "Stage-specific oligonucleotide uptake in murine bone marrow B-cell precursors," Blood 84(11):3660-3666 (1994).

Zheng et al., J. Virol. 75(20):9828-9835, (2001).

Zheng, et al., "Contribution of Vascular Endothelial Growth Factor in the Neovascularization Process During the Pathogenesis of Herpetic Stromal Keratitis," J. Vriol. 75(20):9828-9835 (2001).

Zheng, et al., "DNA containing CpG motifs induces angiogenesis," PNAS, 99(13):8944-8949 (Jun. 25, 2002).

Zhu, et al., "Macaque blood-derived antigen-presenting cells elicit SIV-specific immune responses," J. Med. Primatol, 29:182-192 (2000).

Zimmermann, et al., "CpG oligodeoxynucleotides trigger protective and curative Thl responses in lethal murine leishmaniasis," J. Immunol., 160:3627-3630 (1998).

Sato et al., "Accelerated Wound Healing Mediated by Activation of Toll-like Receptor 9," Wound Repair and Regeneration pp. 1-8 (2010).

* cited by examiner

Figure 1A. Normal Human Broncheal Epithelial cell migration and wound repair
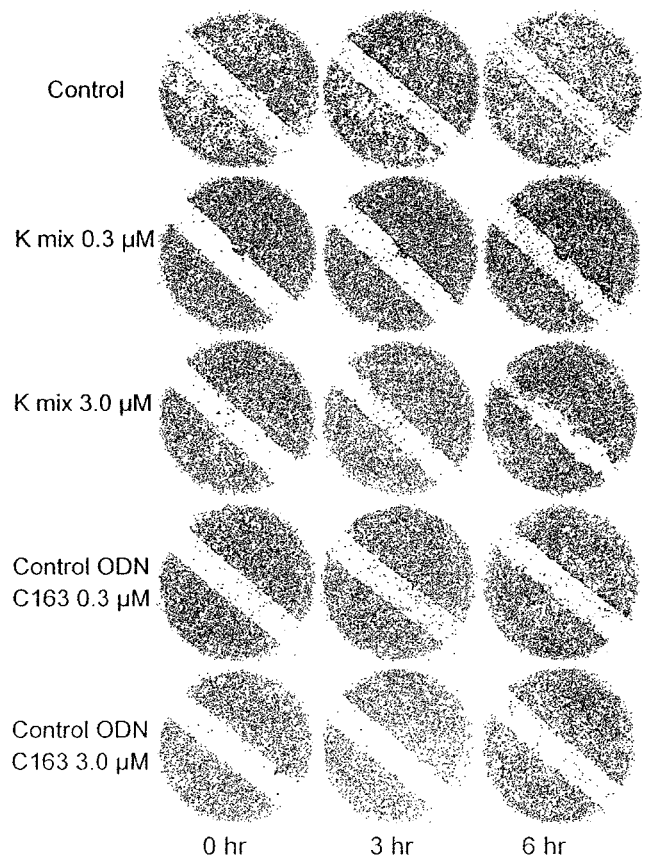
Figure 1B. Analysis of % repair in Normal Human Broncheal Epithelial cells
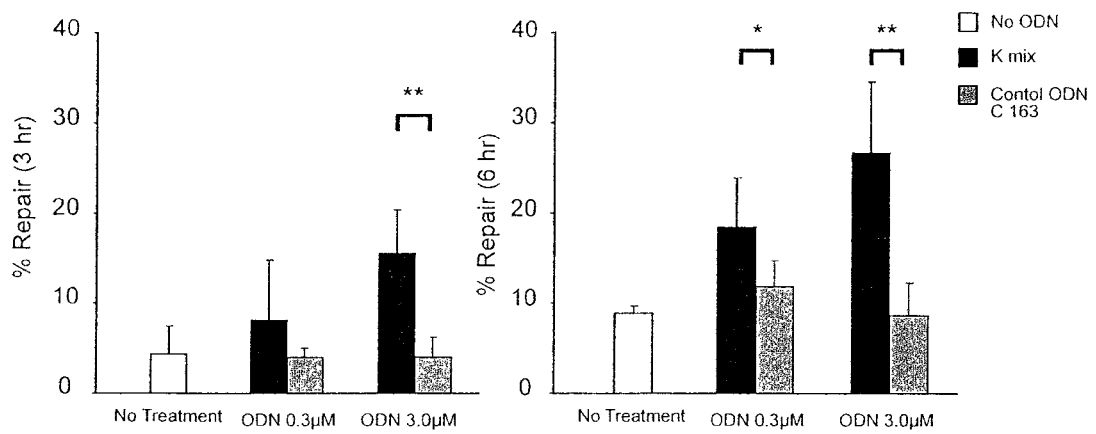

Figure 2A. MM14.Lu cell (Murine lung cell line) migration and wound repair
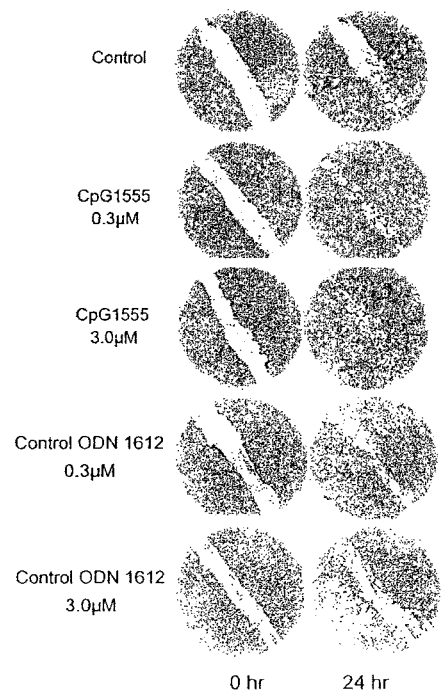
Figure 2B. Analysis of % repair in MM14.Lu cells
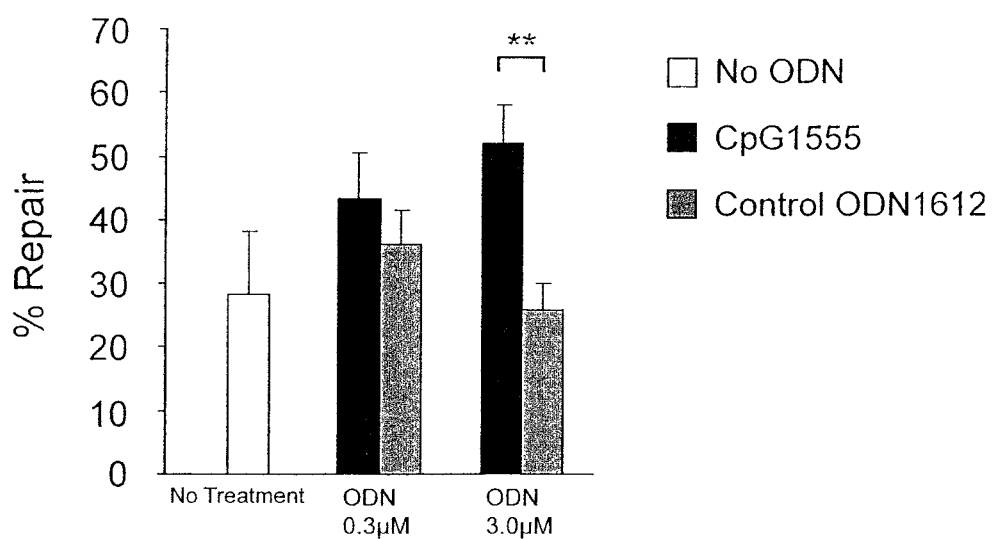

Figure 3. New *in vitro* wound repair assay unit, showing lower and upper compartment, microporous membrane.
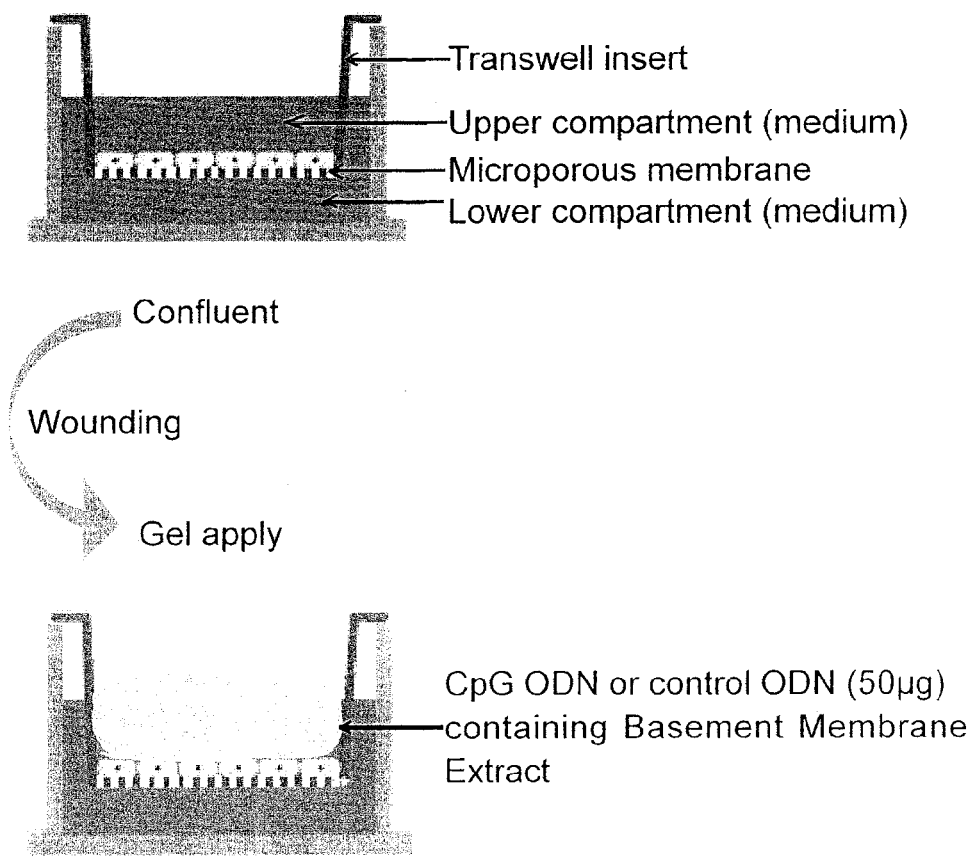

Figure 4A. MM14.Lu cell (murine lung cell line) migration and wound repair
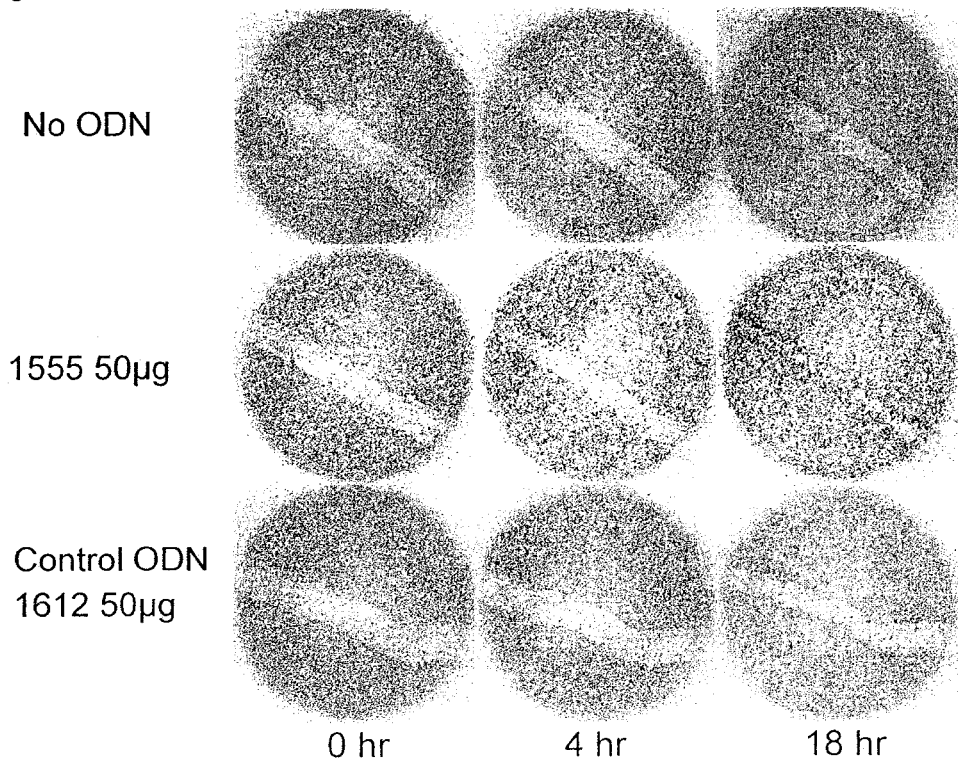
Figure 4B. Analysis of % repair in MM14.Lu cells
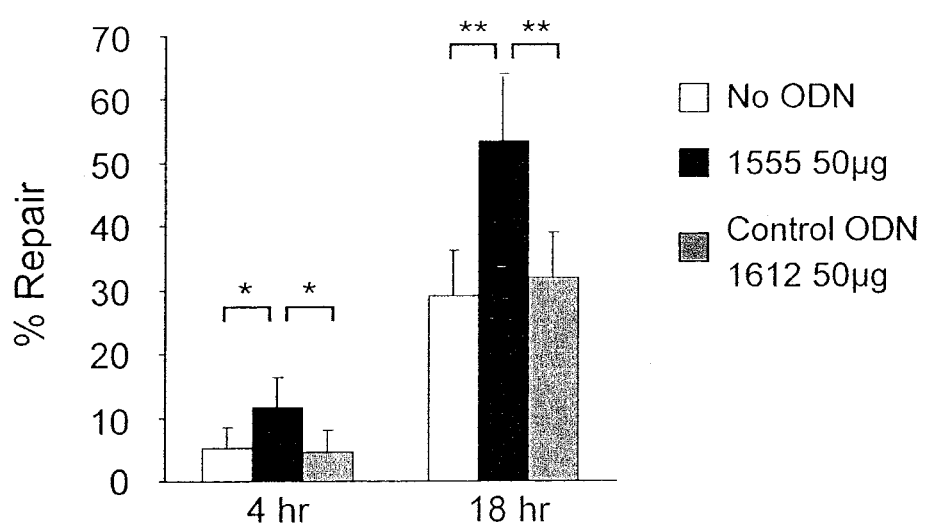

Figure 5. CpG induced NO production in Normal Human Bronchial Epithelial Cells.
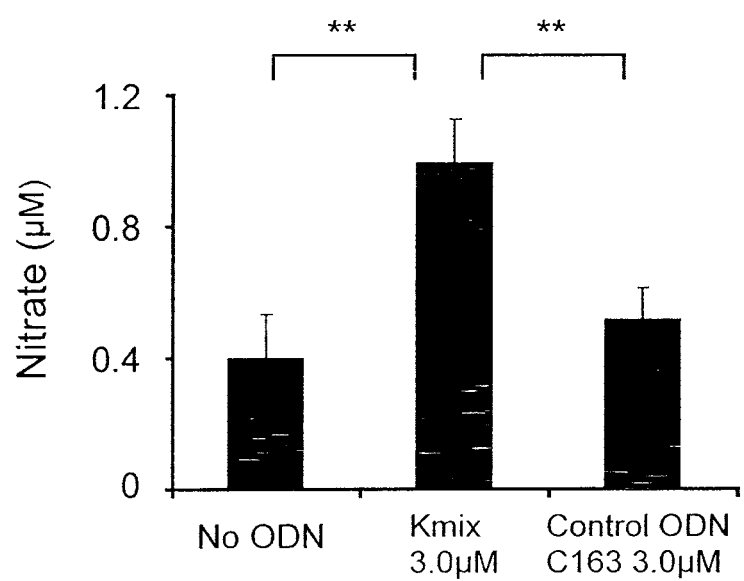

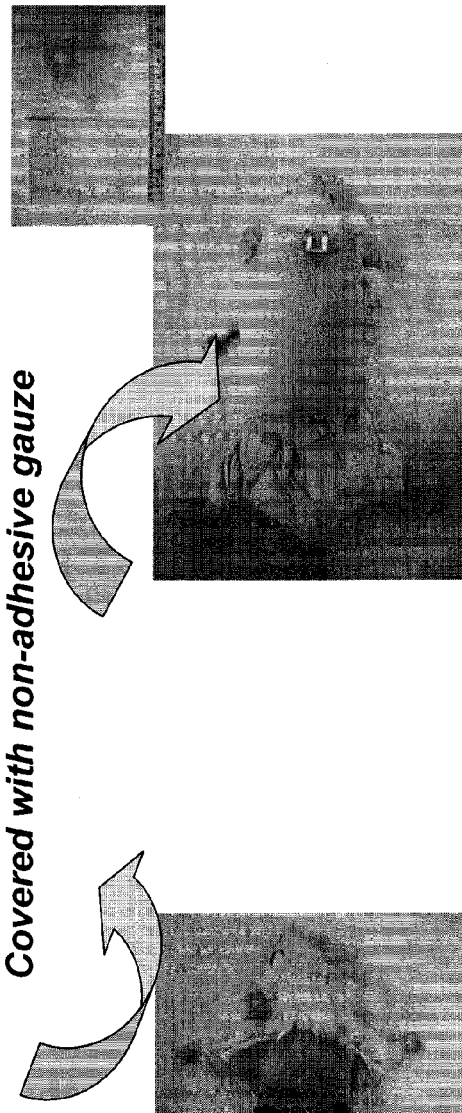
FIG. 6

Effects of CpG-BME gel on murine wound healing model

USE OF CPG OLIGODEOXYNUCLEOTIDES TO INDUCE EPITHELIAL CELL GROWTH

PRIORITY CLAIM

This claims the benefit of U.S. Provisional Application No. 60/970,145, filed Sep. 5, 2007. This is also a continuation-in-part of U.S. application Ser. No. 10/499,597, filed Jun. 17, 2004, now issued as U.S. Pat. No. 7,615,227, which is the §371 U.S. National Stage of International Application No. PCT/US02/40955, filed Dec. 19, 2002, which was published in English under PCT Article 21 (2), which in turn claims the benefit of U.S. Provisional Application No. 60/343,457, filed Dec. 20, 2001. The prior applications are incorporated by reference in their entirety, and priority to them is claimed.

FIELD

This application relates to the field of epithelial cell growth, more specifically to the use of CpG oligodeoxynucleotides to promote wound healing.

BACKGROUND

Wound repair is the result of complex interactions and biologic processes. Three phases have been described in normal wound healing: acute inflammatory phase, extracellular matrix and collagen synthesis, and remodeling (Peacock, E. E., Jr., Wound Repair, 2nd edition, W B Saunders, Philadelphia (1984)). The process involves the interaction of keratinocytes, fibroblasts and inflammatory cells at the wound site. The sequence of the healing process is initiated during an acute inflammatory phase with the deposition of provisional tissue. This is followed by re-epithelialization, collagen synthesis and deposition, fibroblast proliferation, and neovascularization, all of which ultimately define the remodeling phase (Clark, R. A. F., J. Am. Acad. Dermatol. 13:701 (1985)). These events are influenced by growth factors and cytokines secreted by inflammatory cells or by the cells localized at the edges of the wound (Assoian et al., Nature 309:804 (1984); Nemeth et al., "Growth Factors and Their Role in Wound and Fracture Healing," Growth Factors and Other Aspects of Wound Healing in Biological and Clinical Implications, New York (1988), pp. 1 17).

Tissue regeneration is believed to be controlled by specific peptide factors which regulate the migration and proliferation of cells involved in the repair process (Barrett, T. B. et al., Proc. Natl. Acad. Sci. USA 81:6772 6774 (1985); Collins, T. et al., Nature 316:748 750 (1985)). Thus, it has been proposed that growth factors will be useful therapeutics in the treatment of wounds, burns and other skin disorders (Rifkin, D. B. and Moscatelli, J. Cell. Biol. 109:1 6 (1989); Sporn, M. B. et al., J. Cell. Biol. 105:1039 1045 (1987); Pierce, G. F. et al., J. Cell. Biochem. 45; 319 326 (1991)). However, there still remains a need for additional methods to accelerate wound healing and tissue repair.

SUMMARY

Methods of increasing epithelial cell growth are disclosed herein. The methods include administering a therapeutically effective amount of a CpG oligodeoxynucleotide (ODN) to induce epithelial cell division. The epithelial cells can be anywhere in the body, such as the skin. The epithelial cells can be in vitro or in vivo. In vivo, epithelial cell growth can be induced with angiogenesis, or in the absence of angiogenesis. In several embodiments, the epithelial cells are at the site of a wound. This disclosure provides a method of inducing production of vascular endothelial growth factor by a cell. The method includes contacting the cell with a CpG oligonucleotide, thereby inducing the production of vascular endothelial growth factor by the cell. The cell can be an epithelial cell.

This disclosure provides methods of inducing wound healing. The method includes treating the wound with a CpG oligonucleotide, thereby inducing wound healing. The wound can be any type of wound, including traumatic or surgical wounds. The CpG ODN can be applied systemically or locally. In several embodiments, the method includes topical application, using an ointment, or transdermal application such as using a patch, of a therapeutically effective amount of a CpG ODN.

The foregoing and other features and advantages will become more apparent from the following detailed description of several embodiments, which proceeds with reference to the accompanying figures.

BRIEF DESCRIPTION OF THE FIGURES

FIGS. 1A-1B are a digital image and a bar graph showing the effect of K ODN on human bronchial epithelial cell migration and wound repair. FIG. 1A is a digital image of normal human bronchial epithelial cell migration and wound repair over time (0 to 6 hours) in response to an individual K ODN (Control ODN C163) and a mixture of K ODNs. FIG. 1B is a bar graph of the repair seen by the human bronchial epithelial cells. The individual K ODN induced repair; use of a mixture of K ODNs increased the amount of repair.

FIGS. 2A-2B are a digital image and a bar graph showing the effect of K ODN on murine lung cell migration and wound repair. FIG. 2A is a digital image of wound repair in response to two concentrations of a K ODN, CpG 1555. FIG. 2B is a bar graph illustrating that the amount of wound repair was concentration dependent.

FIG. 3 is a schematic diagram showing the in vitro approach used for evaluating topical gels including K ODN.

FIGS. 4A-4B are a digital image and a bar graph showing the effect of CpG ODN 1555 or control ODN 1612 on epithelial cell migration and wound repair over time. Note that the CpG ODNs was significantly more effective at inducing epithelial migration and wound repair than the control ODN.

FIG. 5 is a bar graph showing the production of nitric oxide in a human epithelial cell culture after treatment with the K ODN mix described in FIG. 1 when compared to control ODN.

FIG. 6 is a schematic diagram of a mouse model of wound healing.

SEQUENCE LISTING

Figure 7:
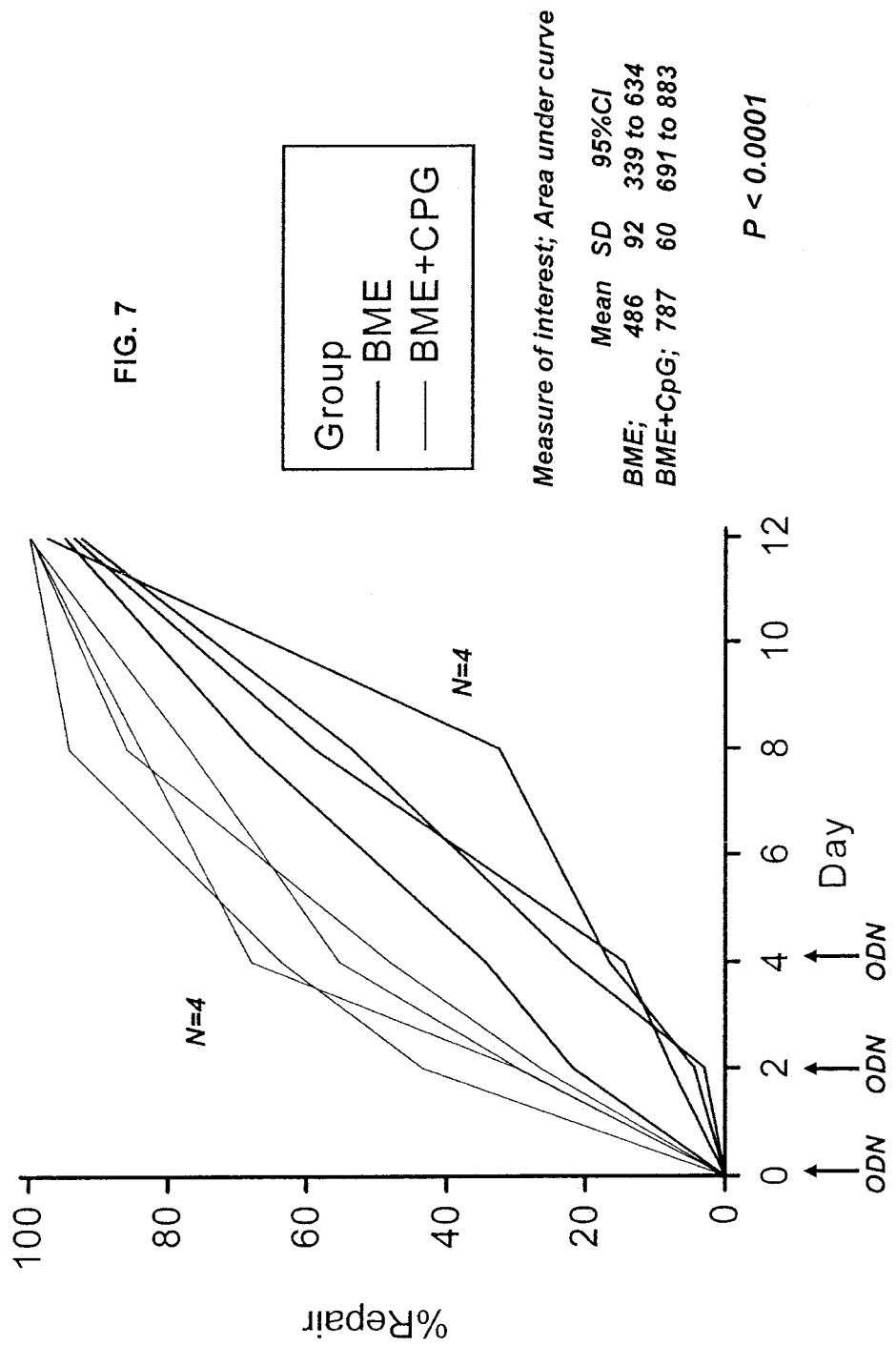
FIG. 7 is a graph of results obtained in the mouse model of wound healing (see FIG. 6). In this system, CpG ODNs were administered at day 0, 2 and 4. Each line represents the results obtained in a single animal model.

The nucleic and amino acid sequences listed in the accompanying sequence listing are shown using standard letter abbreviations for nucleotide bases, and three letter code for amino acids, as defined in 37 C.F.R. 1.822. In the accompanying sequence listing:

SEQ ID NO: 1 is the nucleic acid sequence of a D ODN.
SEQ ID NO: 2 is the nucleic acid sequence of a K ODN.
SEQ ID NOs: 3-31 are the nucleic acid sequences of examples of K ODN.
SEQ ID NOs: 32-33 are the nucleic acid sequence of exemplary control ODN.

DETAILED DESCRIPTION

I. Abbreviations

| | |
|---|---|
| Ab: | antibody |
| BME: | basal membrane extract |
| CpG ODN: | an oligodeoxynucleotide (either a D or a K type) including a CpG motif, as defined herein. |
| mm: | millimeter |
| mRNA: | messenger ribonucleic acid. |
| ODN: | oligodeoxynucleotide |
| µg: | microgram |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. In case of conflict, the present specification, including explanations of terms, will control. In addition, the materials, methods, and examples are illustrative only and not intended to be limiting.

In order to facilitate review of the various embodiments of the invention, the following explanations of specific terms are provided:

Amplification: Of a nucleic acid molecule (such as a DNA or RNA molecule) refers to use of a technique that increases the number of copies of a nucleic acid molecule in a specimen. An example of amplification is the polymerase chain reaction, in which a biological sample collected from a subject is contacted with a pair of oligodeoxynucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligodeoxynucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134. Amplification reactions can be used to produce CpG ODN.

Animal: Living multi-cellular vertebrate organisms, a category that includes, for example, mammals and birds. The term mammal includes both human and non-human mammals. Similarly, the term "subject" includes both human and veterinary subjects.

Angiogenesis: Process leading to the generation of new blood vessels through sprouting from already existing blood vessels. The process involves the migration and proliferation of endothelial cells from preexisting vessels. Angiogenesis occurs both during pre-natal development, post-natal development, and in the adult. In the adult, angiogenesis occurs during the normal cycle of the female reproductive system, wound healing, and during pathological processes such as cancer (for review see Battegay, *J. Molec. Med.* 73(7):333-346, 1995; Beck and D'Amore, *FASEB J.* 11(5):365, 1997). "Neovascularization" is development of new blood vessels in a tissue.

Basal Membrane and Basal Membrane extract: Basement membranes are sheets of extracellular matrix found at the base of all lumen-lining epithelial and endothelial cells. They are generally comprised of basement membrane proteins, including collagen IV, laminin I, heparan sulfate proteoglycan and entactin. Basement Membrane Extract can be used for promotion and maintenance of a differentiated phenotype in a variety of cell cultures including primary epithelial cells, endothelial cells, and smooth muscle cells. It has been employed in angiogenesis assays, tumor cell invasion assays, and as a vehicle to augment the tumorigenicity of injected tumor cells in nude mice. BME is available commercially as MATRIGEL® and CULTREX®, amongst others. One known basement membrane complex, is disclosed in U.S. Pat. No. 4,829,000 to Kleinman et al., and is commercially available as MATRIGEL®, from BD Biosciences of San Jose, Calif. Membrane components extracted from a spontaneous mouse tumor, the Engelbreth-Holm-Swarm (EHS) tumor have been used for studying both two dimensional and three dimensional cell-matrix interactions. It is used routinely in labs throughout the world for studies of basement membrane-cell interactions, angiogenesis (in vitro and in vivo), tumor invasion, and as a scaffold for tissue engineering applications. Another method, as taught in U.S. Pat. No. 5,147,782 to Brocks et al., extracts basement membrane components from human and animal tissues in the presence of a chelating agent. Synthetic matrices are also commercially available, such as PURAMATRIX™ from BD Biosciences and CYTOMATRIX™, from Cytomatrix, LLC.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring at the 5-position of the pyrimidine ring. A CpG oligodeoxynucleotide is an oligodeoxynucleotide that is at least about ten nucleotides in length and includes an unmethylated CpG. CpG oligodeoxynucleotides include both D and K type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

D Type Oligodeoxynucleotide (D ODN): A D type ODN is at least about 16 nucleotides in length, such as 16 to 30 nucleotides in length, and includes a sequence represented by the following formula:

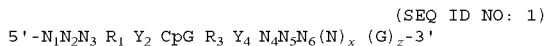
(SEQ ID NO: 1)
5'-N₁N₂N₃ R₁ Y₂ CpG R₃ Y₄ N₄N₅N₆(N)ₓ (G)_z-3' wherein the central CpG motif is unmethylated, R is a purine nucleotide, Y is a pyrimidine nucleotide, N is any nucleotide, X is any integer from 0 to 10, and Z is any integer from 4 to 10. Additional detailed description of D ODN sequences and their activities can be found in Verthelyi et al., *J. Immunol.* 166:2372-2377, 2001, which is herein incorporated by reference. Generally D ODNs can stimulate a cellular immune response.

Epithelial Cell: A closely packed cell that forms an epithelium, such as in the skin. There are several types of epithelium, including simple squamous epithelium, simple cuboidal epithelium, simple columnar epithelium, pseudostratified columnar epithelium, stratified squamous (nonkeratinized) epithelium, stratified cuboidal epithelium, and transitional epithelium.

Isolated: An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

K Type Oligodeoxynucleotide (K ODN): An oligodeoxynucleotide including an unmethylated CpG motif that has a sequence represented by the formula:

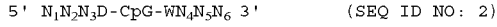
5' N₁N₂N₃D-CpG-WN₄N₅N₆ 3'    (SEQ ID NO: 2)

wherein the central CpG motif is unmethylated, D is T, G or A, W is A or T, and N₁, N₂, N₃, N₄, N₅, and N₆ are any nucleotides. In one embodiment, D is a T. Additional detailed description of K ODN sequences and their activities can be found in the description below. Generally K ODNs can stimulate a humoral response. For example, K ODNs stimulate the production of immunoglobulins, such as IgM and IgG. K ODNs can also stimulate proliferation of peripheral blood mononuclear cells and increase expression of IL-6 and/or IL-12, amongst other activities. In several embodiments, K ODN are about 10 to about 30 nucleotides in length.

Mammal: This term includes both human and non-human mammals. Similarly, the term "subject" includes both human and veterinary subjects.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA, oligodeoxynucleotides or RNA, oligoribonucleotides) which is at least six nucleotides, for example at least 10, 15, 50, 100 or even 200 nucleotides long.

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," "CpG ODN," refers to an oligodeoxynucleotide, which contains a cytosine, guanine dinucleotide sequence. In one embodiment, CpG ODN stimulates (e.g. has a mitogenic effect or induces cytokine production) vertebrate immune cells. CpG ODN can also stimulate angiogenesis. The cytosine, guanine is unmethylated. This includes K and D ODN.

An "oligonucleotide delivery complex" is an oligonucleotide associated with (e.g. ionically or covalently bound to; or encapsulated within) a targeting means (e.g. a molecule that results in a higher affinity binding to a target cell (e.g. B cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Generally, the complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167: 3324, 2001)

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence, if the promoter affects the transcription or expression of the coding sequence. Generally, operably linked DNA sequences are contiguous and, where necessary to join two protein coding regions, in the same reading frame.

Pharmaceutical agent or drug: A chemical compound, nucleic acid molecule, or composition capable of inducing a desired therapeutic or prophylactic effect when properly administered to a subject. In one embodiment, a pharmaceutical agent induces angiogenesis or the production of VEGF.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the oligodeoxynucleotides herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. Acceptable carriers also include creams and ointments, such as for topical administration.

Polynucleotide: A linear nucleic acid sequence of any length. Therefore, a polynucleotide includes molecules which are 10, 15, 50, 100, 200 (oligonucleotides) and also nucleotides as long as a full length cDNA.

Purified: The term purified does not require absolute purity; rather, it is intended as a relative term. Thus, for example, a purified oligonucleotide preparation is one in which the oligodeoxynucleotide is more enriched than the protein is in its generative environment, for instance within a cell or in a biochemical reaction chamber. Preferably, a preparation of oligodeoxynucleotide is purified such that the oligodeoxynucleotide represents at least 50% of the total nucleotide content of the preparation.

Therapeutically effective dose: A dose sufficient to induce epithelial growth, or promote wound healing. In one embodiment, a therapeutically effective dose is an amount sufficient to produce increased division or survival of epithelial cells or is sufficient to promote survival of a graft or cells transplanted into a subject.

Topical application: A topically applied agent, such as the disclosed K-type ODN; is applied only in a specific area, and not throughout the body. In particular examples the K-ODN is applied to the skin in an area where re-epithelialization is desired. For example the K ODN is applied in a topical preparation to a wound, such as an epithelial wound or defect, for example a traumatic or surgical wound, such as an abrasion or surgical incision.

Vascular Endothelial Growth Factor (VEGF): VEGF is a homodimeric heavily glycosylated protein of 46-48 kDa (24 kDa subunits). Glycosylation is not required, however, for biological activity. The subunits are linked by disulphide bonds. The human factor occurs in several molecular variants of 121 (VEGF-121), 165 (VEGF-165), 183 (VEGF-183), 189 (VEGF-189), 206 (VEGR-206) amino acids, arising by alternative splicing of the mRNA (for review see Neufeld et al., *FASEB J.* 13:9, 1999)

The human gene encoding VEGF has a length of approximately 12 kb and contains eight exons. Four species of mRNA encoding VEGF have been identified and found to be expressed in a tissue-specific manner. They arise from differential splicing with the 165 amino acid form of VEGF lacking sequences encoded by exon 6 and the 121 amino acid form lacking exon 6 and 7 sequences. The VEGF gene maps to human chromosome 6p12-p21.

VEGF is a highly specific mitogen for vascular endothelial cells. In vitro the two shorter forms of VEGF stimulate the proliferation of macrovascular endothelial cells. VEGF does not appear to enhance the proliferation of other cell types. VEGF significantly influence vascular permeability and is a strong angiogenic protein in several bioassays and probably also plays a role in neovascularization under physiological conditions. A potent synergism between VEGF and beta-FGF in the induction of angiogenesis has been observed. It has been suggested that VEGF released from smooth muscle cells and macrophages may play a role in the development of arteriosclerotic diseases.

VEGF can be assayed by an immunofluorometric test. An alternative and entirely different detection method is RT-PCR quantitation of cytokines. Methods for performing these assays are known (e.g. see Yeo et al., *Clinical Chem.* 38:71, 1992).

CpG ODN

A CpG oligodeoxynucleotide is an oligodeoxynucleotide including a CpG motif, wherein the pyrimidine ring of the cytosine is unmethylated. Two types of CpG ODNs have been identified: K type and D type ODNs. In one embodiment, the CpG ODN is in the range of about 8 to 30 nucleotides in length. In another embodiment, the CpG ODN is at least 10 nucleotides in length, such as about 10 to about 30 nucleotides in length. For use in the methods disclosed herein, the nucleic acids can be synthesized de novo using any of a number of procedures well known in the art. For example, the b-cyanoethylphosphoramidite method (Beaucage et al., *Tet. Let.* 22:1859, 1981) or the nucleoside H-phosphonate method (Garegg et al., *Tet. Let.* 27:4051, 1986; Froehler et al., *Nucl. Acid Res.* 14:5399, 1986; Garegg et al., *Tet. Let.* 27:4055, 1986; Gaffney et al., *Tet. Let.* 29:2619, 1988) can be utilized. These chemistries can be performed by a variety of automated oligonucleotide synthesizers available in the market.

Alternatively, CpG dinucleotides can be produced on a large scale in plasmids, (see Sambrook, et al., *Molecular Cloning: A Laboratory Manual*, Cold Spring Harbor Laboratory Press, New York, 1989) which after being administered to a subject are degraded into oligonucleotides. Oligonucleotides can be prepared from existing nucleic acid sequences (e.g., genomic or cDNA) using known techniques, such as those employing restriction enzymes, exonucleases or endonucleases (see PCT Application No. PCT/US98/03678).

For use in vivo, nucleic acids can be utilized that are relatively resistant to degradation (such as by endo- and exonucleases). Secondary structures, such as stem loops, can stabilize nucleic acids against degradation. Alternatively, nucleic acid stabilization can be accomplished via phosphate backbone modifications. In one embodiment, a stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made (e.g., as described in U.S. Pat. No. 4,469,863) and alkylphosphotriesters (in which the charged oxygen moiety isalkylated, as described in U.S. Pat. No. 5,023,243 and European Patent No. 092,574), and can be prepared by automated solid phase synthesis using commercially available reagents.

In one embodiment, the phosphate backbone modification occurs at the 5' end of the nucleic acid. One specific, non-limiting example of a phosphate backbone modification is at the first two nucleotides of the 5' end of the nucleic acid. In another embodiment, the phosphate backbone modification occurs at the 3' end of the nucleic acid. One specific, non-limiting example of a phosphate backbone modification is at the last five nucleotides of the 3' end of the nucleic acid.

Methods for making other DNA backbone modifications and substitutions have been described (Uhlmann et al., *Chem. Rev.* 90:544, 1990; Goodchild, *Bioconjugate Chem.* 1:1, 1990). 2'-O-methyl nucleic acids with CpG motifs also cause angiogenesis, as do ethoxy-modified CpG nucleic acids. In fact, no backbone modifications have been found that completely abolish the CpG effect, although it is greatly reduced by replacing the C with a 5-methyl C.

For administration in vivo, nucleic acids may be associated with a molecule that results in higher affinity binding to target cell (such as an epithelial cell) surfaces and/or increased cellular uptake by target cells to form a "nucleic acid delivery complex." Nucleic acids can be ionically or covalently associated with appropriate molecules using techniques which are well known in the art (see below). Nucleic acids can alternatively be encapsulated in liposomes or virosomes using well-known techniques.

D and K type nucleic acids sequences of use are described in the published PCT Applications No. WO 98/18810A1 (K-type) and WO 00/61151 (D-type), which are incorporated by reference herein in their entirety. Generally, only K ODNs are used in the methods disclosed herein. Thus, in several embodiments, the methods do not include the use of D type ODNs. Combinations of K type ODNs are of use, such as the use of at least two, at least three, at least four, at least five, at least six at least seven, at least eight or at least ten ODNs, each with a different nucleic acid sequence. In several embodiments, two, three, four, five or six K type ODNs, each with a different nucleic acid sequence, are utilized in the methods.

A CpG ODN can be associated with (for example, ionically or covalently bound to, or encapsulated within) a targeting moiety. Targeting moieties include any a molecule that results in higher affinity binding to a target cell, such as, but not limited to, an endothelial cell.

A variety of coupling or cross-linking agents can be used to form the delivery complex, such as protein A, carbodiamide, and N-succinimidyl (2-pyridyldithio) propionate (SPDP). Examples of delivery complexes include CpG ODNs associated with a sterol (such as cholesterol), a lipid (such as a cationic lipid, virosome or liposome), and a target cell specific binding agent (such as a ligand recognized by target cell specific receptor). In one embodiment, the complexes are sufficiently stable in vivo to prevent significant uncoupling prior to internalization by the target cell. However, these complexes can be cleavable under appropriate circumstances such that the oligodeoxynucleotide can be released in a functional form (see WO 00/61151).

A single K ODN can be used in the methods disclosed herein, or mixtures of K ODN can also be used in the methods disclosed herein. Specific combinations of ODNs are disclosed, for example, in U.S. patent application Ser. No. 10/194,035, which is incorporated herein by reference.

K ODN

In several embodiments, a K type ODN or a mixture of K type ODNs are utilized. Briefly, the K type nucleic acid sequences useful in the methods disclosed herein are represented by the formula:

5'-N$_1$DCGYN$_2$-3' wherein at least one nucleotide separates consecutive CpGs; D is adenine, guanine, or thymidine; Y is cytosine or thymine; N is any nucleotide and N$_1$+N$_2$ is from about 0-26 bases. In one embodiment, N$_1$ and N$_2$ do not contain a CCGG quadmer or more than one CGG trimer; and the nucleic acid sequence is from about 8-30 bases in length, such as about 10 to 30 nucleotides in length. However, nucleic acids of any size (even many kb long) can be used in the methods disclosed herein if CpGs are present. In one embodiment, synthetic oligonucleotides of use do not include a CCGG quadmer or more than one CCG or CGG trimer at or near the 5' or 3' terminals and/or the consensus mitogenic CpG motif is not a palindrome. A "palindromic sequence" or "palindrome" means an inverted repeat (i.e., a sequence such as ABCDEE'D'C'B'A', in which A and A' are bases capable of forming the usual Watson-Crick base pairs).

In another embodiment, the methods include the use of an oligodeoxynucleotide which contains a CpG motif represented by the formula:

5'-N$_1$RDCGYTN$_2$-3' wherein at least one nucleotide separates consecutive CpGs; RD is selected from the group consisting of GpT, GpG, GpA, ApT and ApA; YT is selected from the group consisting of TpT or CpT; N is any nucleotide and N$_1$+N$_2$ is from about 0-26 bases, such that the ODN is about 8 to 30 nucleotides in length.

In several embodiments, the methods disclosed herein include the use of an effective amount of at least one K ODN, wherein the K ODN9s) include an unmethylated CpG motif that has a sequence represented by the formula:

5' N$_1$N$_2$N$_3$D-CpG-WN$_4$N$_5$N$_6$ 3'     (SEQ ID NO: 2)

wherein the central CpG motif is unmethylated, D is T, G or A, W is A or T, and N$_1$, N$_2$, N$_3$, N$_4$, N$_5$, and N$_6$ are any nucleotides. In one embodiment, D is a T. The K ODN(s) can be 10 to 30 nucleotides in length. A K ODN can include multiple CpG motifs. In some embodiments, at least one nucleotide separates consecutive CpGs; N$_3$D is selected from the group consisting of GpT, GpG, GpA, ApT and ApA; WN$_4$ is selected from the group consisting of TpT or CpT; N is any nucleotide and N$_1$+N$_2$ is from about 0-26 bases In one embodiment, N$_1$, and N$_2$ do not contain a CCGG quadmer or more than one CCG or CGG trimer. CpG ODN are also in the range of 8 to 30 bases in length, but may be of any size (even many kb long) if sufficient motifs are present. In several examples, the CpG ODN is 10 to 20 nucleotides in length, such as 12 to 18 nucleotides in length. In one embodiment, synthetic oligodeoxynucleotides of this formula do not include a CCGG quadmer or more than one CCG or CGG trimer at or near the 5' and/or 3' terminals and/or the consensus CpG motif is not a palindrome. Other CpG oligodeoxynucleotides can be assayed for efficacy using methods described herein. It should be noted that exemplary K ODNs are known in the art, and have been fully described, for example in PCT Publication No. WO 98/18810A1, which is incorporated herein by reference.

Exemplary K ODN are listed below

| K ODN | | | |
|---|---|---|---|
| K X | 5'-ATAATCGACGTTCAAGCAAG-3'. | (SEQ ID NO: 3) |
| K22 | CTCGAGCGTTCTC | (SEQ ID NO: 4) |
| K21 | TCTCGAGCGTTCTC | (SEQ ID NO: 5) |
| K82 | ACTCTGGAGCGTTCTC | (SEQ ID NO: 6) |

-continued

| K30 | TGCAGCGTTCTC | (SEQ ID NO: 7) |
| k31 | TCGAGGCTTCTC | (SEQ ID NO: 8) |
| K39 | GTCGGCGTTGAC | (SEQ ID NO: 9) |
| K16 | TCGACTCTCGAGCGTTCTC | (SEQ ID NO: 10) |
| K3 | ATCGACTCTCGAGCGTTCTC | (SEQ ID NO: 11) |
| k23 | TCGAGCGTTCTC | (SEQ ID NO: 12) |
| K40 | GTCGGCGTCGAC | (SEQ ID NO: 13) |
| K34 | GTCGACGTTGAC | (SEQ ID NO: 14) |
| K83 | ACTCTCGAGGGTTCTC | (SEQ ID NO: 15) |
| K19 | ACTCTCGAGCGTTCTC | (SEQ ID NO: 16) |
| K73 | GTCGTCGATGAC | (SEQ ID NO: 17) |
| K46 | GTCGACGCTGAC | (SEQ ID NO: 18) |
| K47 | GTCGACGTCGAC | (SEQ ID NO: 19) |
| K72 | GTCATCGATGCA | (SEQ ID NO: 20) |
| K37 | GTCAGCGTCGAC | (SEQ ID NO: 21) |
| k25 | TCGAGCGTTCT | (SEQ ID NO: 22) |
| K82 | ACTCTGGAGCGTTCTC | (SEQ ID NO: 23) |
| K83 | ACTCTCGAGGGTTCTC | (SEQ ID NO: 24 |
| K84 | ACTCTCGAGCGTTCTA | (SEQ ID NO: 25) |
| K85 | CATCTCGAGCGTTCTC | (SEQ ID NO: 26) |
| K89 | ACTCTTTCGTTCTC | (SEQ ID NO: 27) |
| K109 | TCGAGCGTTCT | (SEQ ID NO: 28) |
| K123 | TCGTTCGTTCTC | (SEQ ID NO: 29) |
| K1555 | GCTAGACGTTAGCGT | (SEQ ID NO: 30) |
| K110 | TCGAGGCTTCTC | (SEQ ID NO: 31) |
| CONTROL | | |
| K1612 | TAGAGCTTAGCTTGC | (SEQ ID NO: 32) |
| C163 | TTGAGTGTTCTC | (SEQ ID NO: 33) |

Exemplary combinations include 1) K3, K19, K110;
2) K19, K23, K123; K3, 3) K110, K123; 4) K3, K23,
K123; 5) K3, K19, K123; and 6) K19, K110, K123.

Additional exemplar combinations include at least
two different K-type ODNS, wherein one of the K
type ODNs is K1555, and/or wherein one of the K
type ODNs is K3.

Pharmacologic Compositions and Therapeutic Use

It is disclosed herein that CpG ODN, such as K ODN and mixtures of at least two, at least three, at least four, at least five or two to five different K ODN can be used to heal wounds, such as dermal wounds, by stimulating epithelial cell proliferation. These wounds may be of superficial nature or may be deep and involve damage of the dermis and the epidermis of skin. Thus, methods are provided to promote wound healing in a subject. The methods include administering a therapeutically effective amount of at least one K ODN to the subject, thereby promoting wound healing. The methods include the use of a therapeutically effective amount of at least one K ODN to promote wound healing in the presence or in the absence of angiogenesis. In one embodiment, administration of at least one K ODN induces production of vascular endothelial growth factor (VEGF) and stimulates epithelial cell proliferation. The at least one K ODN can be administrated either systemically (for example, remote from the target) location where epithelial cell proliferation is desired, or it can be applied directly to the target location, for example in a topical preparation such as an ointment, cream, liquid, salve or as a part of a dressing or a bandage.

The subject can be any mammalian subject of interest, including a human or a veterinary subject. The subject can be a child or an adult subject, such as a young, middle aged, or older adult subject. In humans, an adult subject is greater than 18 years of age, a young adult is about 18 to about 35 years of age, a middle aged adult is generally considered to be about 35 to about 55 years of age, and an elderly (or aged) human subject is more than about 55 years old, such as more than 60 years old, more than 65 years old, more than 70 years old, more than 75 years old or more than 80 years old. In mice, older animals are generally more than about 16 months old.

The subject can heal wounds at a normal rate or can be healing impaired. When administered to an individual who is not healing impaired, a therapeutically effective amount of at least one K ODN is administered to accelerate the normal healing process. When administered to an individual who is healing impaired, a therapeutically effective amount of at least one K ODN is administered to facilitate the healing of wounds which would otherwise heal slowly (or not at all) without treatment. A number of afflictions and conditions can result in healing impairment. These include diabetes (such as Type II diabetes mellitus), treatment with both steroids and other pharmacological agents, and ischemic blockage or injury (as in peripheral vascular disease or traumatic vascular occlusion). Conditions which induce abnormal wound healing, include, but are not limited to uremia, malnutrition, vitamin deficiencies, obesity, infection, immunosuppression and complications associated with systemic treatment with steroids, radiation therapy, and antineoplastic drugs and antimetabolites. Steroids which have been shown to impair wound healing include cortisone, hydrocortisone, dexamethasone, and methylprednisolone. Non-steroid compounds, such as ocreotide acetate, have also been shown to impair wound healing (Waddell et al., Am. Surg. 63:446 449, 1997). Thus, the methods disclosed herein are of use to promote wound healing in a subject has impaired wound healing due to disease or due to treatment with a pharmaceutical agent that has the side effect of decreasing wound healing. The methods can include selecting the subject with impaired wound healing, such as a subject with one of the conditions listed above.

Methods are provided for promoting the healing of anastomotic and other wounds caused by surgical procedures in individuals. These methods include administration of an effective amount of at least one K ODN to an individual before, after, and/or during anastomotic or other surgery. Anastomosis is the connecting of two tubular structures, for example, when a mid-section of intestine is removed and the remaining portions are linked together to reconstitute the intestinal tract. Unlike cutaneous healing, the healing process of anastomotic wounds is generally obscured from view. Further, wound healing, at least in the gastrointestinal tract, occurs rapidly in the absence of complications; however, complications often require correction by additional surgery. Thornton, F. and Barbul, A., Surg. Clin. North Am. 77:549 573 (1997). The method can include selecting a subject in need of anastomotic wound healing. The subject can be a subject with impaired wound healing due to one of the conditions above, or can be a subject that has normal wound healing, such as a subject that does not have any of the conditions listed above.

Methods are also provided for stimulating healing of wounds including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, and burns resulting from heat exposure or chemicals. Methods are also provided for wounds that result from ischemia and ischemic injury, such as chronic venous leg ulcers caused by an impairment of venous circulatory system return and/or insufficiency. A therapeutically effective amount of at least one K ODN can be used to promote dermal reestablishment subsequent to dermal loss. In addition, a therapeutically effective amount of at least one K ODN can be used to increase the tensile strength of epidermis and epidermal thickness. Thus, the disclosed methods are of use in stimulating the healing of different types of wounds in normal subjects and subjects that have impaired wound healing.

Methods are also provided herein to increase the adherence of skin grafts to a wound bed and to stimulate re-epithelialization from the wound bed. Types of grafts include, but are not limited to: autologous skin graft, artificial skin, allografts, autodermic graft, autoepidermic grafts, avascular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The methods include administering to the subject with the graft a therapeutically effective amount of at least one K ODN, thereby increasing the adherence and acceptance of the graft. In some embodiments, cells or a tissue treated with CpG ODN are transplanted into a subject. In one specific, non-limiting example, CpG ODNs are administered to a graft, such as a skin graft, prior to transplantation.

Methods are also provided to treat blisters and burns due to abrasion or chemical injury. These methods include the treatment of the skin or internal organs. These methods include treatment of ovary injury, for example, due to treatment with chemotherapeutics or treatment with cyclophosphamide; radiation- or chemotherapy-induced cystitis; or high-dose chemotherapy-induced intestinal injury. The methods include administering to the subject a therapeutically effective amount of at least one K ODN to promote healing of the blisters or burns.

It is disclosed herein that administration of a K ODN to lung epithelial cells stimulates proliferation of lung epithelial cells. Thus, a therapeutically effective amount of at least one K ODN can be administered prophylactically to reduce or prevent damage to the lungs caused by various pathological states. For example, a therapeutically effective amount of at least one K ODN can be used to induce proliferation and differentiation and promote the repair of alveoli and bronchiolar epithelium to prevent, attenuate, or treat acute or chronic lung damage. Thus, methods are provided for the treatment of inhalation injuries, such as resulting from smoke or chemical inhalation and burns, that cause necrosis of the bronchiolar epithelium and alveoli. Methods are also provided for the treatment of damage to the lung epithelium attributable to chemotherapy, radiation treatment, lung cancer, asthma, black lung and other lung damaging condition.

In one embodiment, a CpG ODN is administered to a cell or a tissue culture in vitro. In another embodiment, cells or a tissue treated with CpG ODN are transplanted into a subject. In one specific, non-limiting example, CpG ODNs are administered to a graft, such as a skin graft, prior to transplantation. In one specific, non-limiting example, CpG ODNs are administered to an organ, such as a heart, lung, or kidney, following transplantation, to promote epithelial cell growth into the transplanted organ.

The CpG ODN can be administered with a basement membrane extract. Suitable basement membrane extracts include a biologically active polymerizable extract containing in parts by weight about 60-85% laminin, 5-30% collagen IV, 1-10% nidogen, 1-10% heparan sulfate proteoglycan and 1-5% entactin (see U.S. Pat. No. 4,829,000, incorporated herein by reference, which discloses BME compositions as well as methods for producing these compositions). BME can support normal growth and differentiation of various cell types including epithelial cells when cultured. Basal membrane extracts are well known in the art and are commercially available.

Growth factors have been shown to promote wound healing, such as in healing impaired individuals (Steed, et al., J. Am. Coll. Surg. 183:6164, 1996; Richard et al., Diabetes Care 18: 64 69, 1995; Steed et al., Vasc. Surg. 21:7178, 1995; Kelley et al., Proc. Soc. Exp. Biol. 194:320 326, 1990). These growth factors include growth hormone-releasing factor (GHRF), platelet-derived growth factor (PDGF), and basic fibroblast growth factor (bFGF or FGF-2). In several embodiments, a therapeutically effective amount of at least one K ODN is administered in conjunction with a growth factor that promotes wound healing. In one embodiment, the CpG ODN is administered with an agent that promotes angiogenesis, such as vascular endothelial growth factor (VEGF).

Nitric oxide has also been shown to play an important role for wound repair from the inflammatory phase to scar remodeling (Schwentker A, et al., Surg. Clin. North Am. 83:521 530, 2003). The local site of nitric oxide is highly coordinated in normal wound healing, thus KODN-mediated induction of nitric oxide in epithelial cells (see, for example, FIG. 5) could promote wound healing, such as in healing impaired individuals.

For treatment of the skin, a therapeutically effective amount of at least one K ODN can be locally administered to the affected area of the skin, such as in the form of an ointment. In one embodiment, the ointment is an entirely homogenous semi-solid external agent with a firmness appropriate for easy application to the skin. Such an ointment can include fats, fatty oils, lanoline, Vaseline, paraffin, wax, hard ointments, resins, plastics, glycols, higher alcohols, glycerol, water or emulsifier and a suspending agent. Using these ingredients as a base, a decoy compound can be evenly mixed. Depending on the base, the mixture can be in the form of an oleaginous ointment, an emulsified ointment, or a water-soluble ointment oleaginous ointments use bases such as plant and animal oils and fats, wax, Vaseline and liquid paraffin. Emulsified ointments are comprised of an oleaginous substance and water, emulsified with an emulsifier. They can take either an oil-in-water form (O/W) or a water-in-oil-form (W/O). The oil-in-water form (O/W) can be a hydrophilic ointment. The water-in-oil form (W/O) initially lacks an aqueous phase and can include hydrophilic Vaseline and purified lanoline, or it can contain a water-absorption ointment (including an aqueous phase) and hydrated lanoline. A water-soluble ointment can contain a completely water-soluble Macrogol base as its main ingredient.

Pharmaceutically acceptable carriers include a petroleum jelly, such as VASELINE®, wherein the petroleum jelly contains 5% stearyl alcohol, or petroleum jelly alone, or petroleum jelly containing liquid paraffin. Such carriers enable pharmaceutical compositions to be prescribed in forms appropriate for consumption, such as tablets, pills, sugar-coated agents, capsules, liquid preparations, gels, ointments, syrups, slurries, and suspensions. When locally administered into cells in an affected area or a tissue of interest, the at least one K ODN can be administered in a composition that contains a synthetic or natural hydrophilic polymer as the carrier. Examples of such polymers include hydroxypropyl cellulose and polyethylene glycol. One or more K ODNs can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used. A therapeutically effective amount of one or more K ODN can also be incorporated into bandages and dressings for wounds.

For administration by inhalation, the K ODN can be conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

Pharmacologically acceptable carriers (e.g., physiologically or pharmaceutically acceptable carriers) are well known in the art, and include, but are not limited to buffered solutions at a physiological pH (e.g. from a pH of about 7.0 to about 8.0, or at a pH of about 7.4). One specific, non-limiting example of a physiologically compatible buffered solution is phosphate buffered saline. Other pharmacologically acceptable carriers include penetrants, which are particularly suitable for pharmaceutical formulations that are intended to be topically applied (for example in the application of surgical wounds to promote healing).

The pharmacological compositions disclosed herein facilitate the use of at least one K ODN, either in vivo or ex vivo, to promote epithelial cell growth and induce wound healing. Such a composition can be suitable for delivery of the active ingredient to any suitable subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically. Proper formulation is dependent upon the route of administration chosen. Thus, for injection, the active ingredient can be formulated in aqueous solutions. For transmucosal administration, penetrants appropriate to the barrier to be permeated are used in the formulation. Such penetrants are generally known in the art.

For oral administration, the active ingredient can be combined with carriers suitable for incorporation into tablets, pills, capsules, liquids, gels, syrups, slurries, suspensions and the like. The active ingredient can be formulated for parenteral administration by injection, such as by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

Optionally, the at least one K ODN can be contained within or conjugated with a protein, hydrocarbon or lipid, whether for in vitro or in vivo administration. Once this molecule is administered, the ODN sequence must be exposed on the surface to induce production of VEGF and/or angiogenesis. The K ODN can also be co-administered with a protein, hydrocarbon, or lipid. Co-administration can be such that the at least one K ODN is administered before, at substantially the same time as, or after the protein, hydrocarbon, or lipid. In one embodiment, the at least one K ODN is administered at substantially the same time, as the protein, hydrocarbon, or lipid.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the at least one K ODN is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation. The delivery system can include collagen, fibrin, or a membrane extract, such as a basal membrane extract.

Use of a long-term sustained release implant may be particularly suitable for treatment of chronic conditions, such as to promote graft survival. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. These systems have been described for use with K ODNs (see U.S. Pat. No. 6,218,371). For use in vivo, nucleic acids are preferably relatively resistant to degradation (such as via endo- and exo-nucleases). Thus, modifications, such as phosphate backbone modifications (see above) can be utilized to promote stabilization.

The therapeutically effective amount of K ODN will be dependent on the ODN utilized, the subject being treated, the severity and type of the affliction, and the manner of administration. For example, a therapeutically effective amount of K ODN can vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound (such as the K ODN utilized), the age, weight, sex and physiological condition of the subject.

The invention is illustrated by the following non-limiting Examples.

EXAMPLES

Example 1

Materials and Methods

Reagents

Phosphorothioate ODNs were synthesized as previously described (Verthelyi et al., *J Immunol.*, 166:2372-2377, 2001). The sequences of the stimulatory ODNs used in this study were: *** a mixture of stimulatory K ODNs, as well as stimulation CpG ODN 1555 alone, and control ODNs C163 and 1612. There was no detectable endotoxin contamination in any of the ODNs, as monitored by LAL assay (Bio Whittaker, Inc., Walkersville, Md.

Experiments were performed on a primary normal human bronchial epithelial cell culture obtained from Cambrex Bio Sciences (Walkersville, Md.) between passage numbers 3 and 5, and immortalized murine lung cell line (MM14.Lu) obtained from American Type Cell Culture (ATCC, Rockville, Md.).

Experiments were performed in 12-well plates with or without Transwell Permeable 0.4 µm PTFE Membrane with collagen coated Insert (Corning, Corning, N.Y.).

Transwell Inserts

MM14.Lu murine cells were grown to confluence on porous membranes in transwell inserts. The cell monolayer was scratched using a sterile P-200 pipette tip followed by removal of the medium. After washing with media to remove cell debris, the cells were then treated on their superficial surface with CpG containing basement membrane extract (see FIG. 3). Wound closure was followed up to 24 hr, using an IX50 inverted microscope (Olympus, Center Valley, Pa.) and was expressed as a percentage of initial wound area (NIH Image J).

Statistical Analysis

Significant differences between groups were evaluated using the Student's t test. $P \leq 0.05$ was regarded as significant difference between two groups. Significant differences between groups were evaluated using one-way analysis of variance (ANOVA) followed by post-hoc analysis with Bonferroni test.

Example 2

K ODN Promotes Wound Healing

The effect of K ODN was demonstrated in two kinds of in vitro assays of wound healing using either normal human bronchial epithelial cells or murine lung cell. As shown in FIGS. 1 and 2, K1555 facilitates repair in a dose-dependent manner. Moreover, K1555-containing gels, prepared for extending the application for in vivo use, also showed significant acceleration of wound healing (FIG. 4). The production of nitric oxide in a human epithelial cell culture after treatment with the K ODN mix is shown in FIG. 5.

Example 3

K ODN Promote Wound Healing In Vivo

The effect of K ODN was further demonstrated in vivo using the model system described by Ishida et al., J Immunol 2008, 180: 569-579 and Macedo et al., Am J Pathol 2007, 171: 1774-1788, both of which are incorporated herein by reference. A schematic diagram of the model system used is shown in FIG. 6. A single dose of antibiotic (kanamycin; 25 units/kg) was administered intramuscularly to all animals approximately 1 hour prior to surgery. All survival surgery was performed using aseptic technique under general anesthesia. An exemplary general anesthetic is ketamine/xylazine (150/8 mg/kg) administered intraperitoneally with additional ketamine (30 mg/kg) given intraperitoneally as needed to maintain deep anesthesia. The dorsal surface of the animals was shaved, and standardized 6 mm skin wounds were excised from the dorsum of each anesthetized mouse. A basal membrane extract (BME) was applied to each wound. The BME was obtained from Trevigen, Inc. (BME Growth Factor Reduced PathClear; Catalog Number 3433-005-02; Lot Number 13238G7). For the experimental animals, a K ODN was included in the BME, while for the control animals no ODN or a control ODN was included in the BME. For each mouse, 50 µl of BME was applied, either with or without 50 µg of CpG or control oligodeoxynucleotide in each dorsal wound at Day 0, 2, and 4. The BME was covered with a non-adhesive gauze, and the animals were wrapped in a coverlet. The wounded mice were unwrapped every other day and treated with BME (with or without K ODN) at day two and day 4. The wounds were serially imaged by digital camera every other day and analyzed by Image J software.

Figure 8:
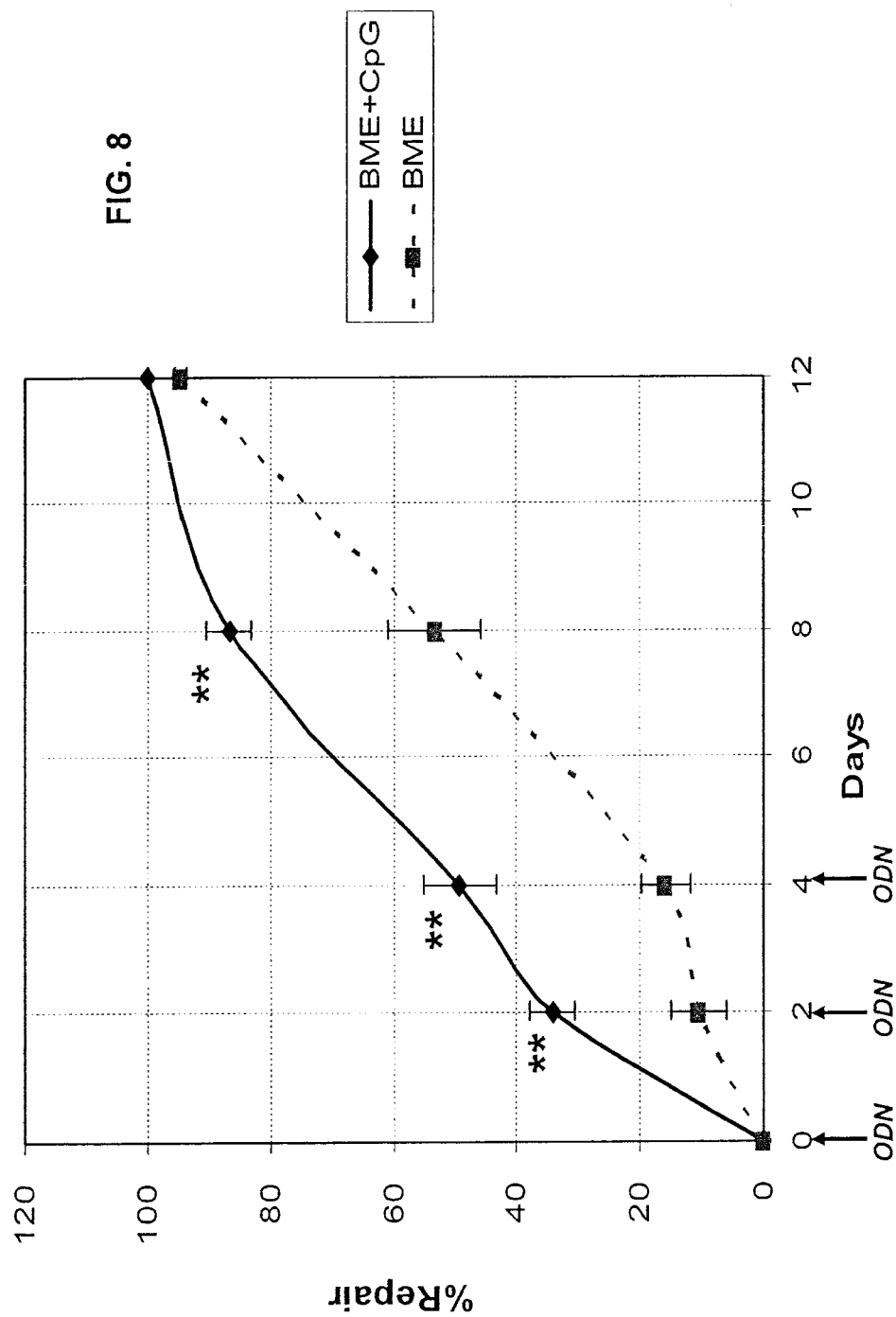
FIG. 8 is a graph of results obtained in the mouse model of wound healing (see FIG. 6), using young mice. In this system, CpG ODNs were administered at day 0, 2 and 4. The results shown are the mean percent repair at each time point.
Figure 9:
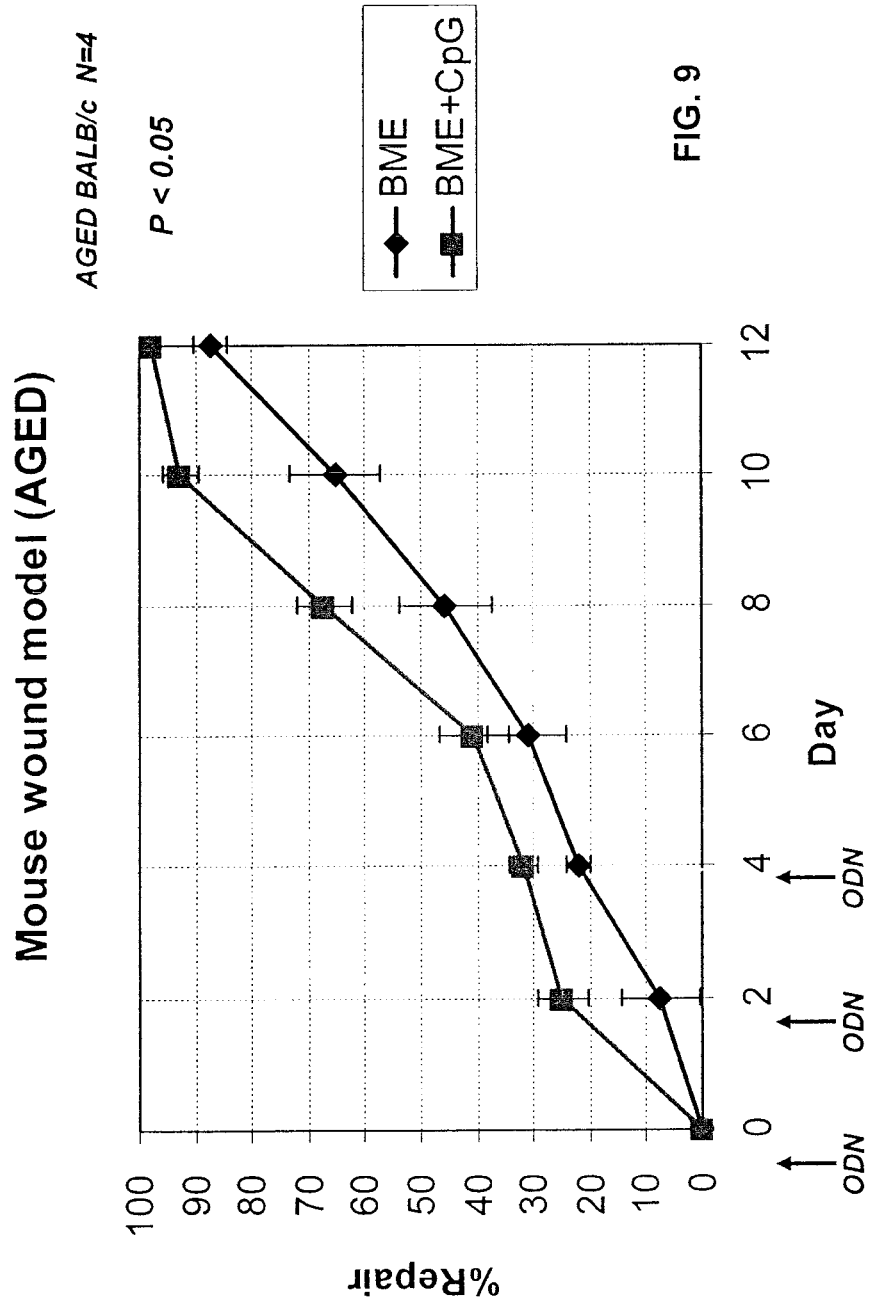
FIG. 9 is a graph of results obtained in the mouse model of wound healing (see FIG. 6), using older mice. In this system, CpG ODNs were administered at day 0, 2 and 4. The results are the mean percent repair at each time point.
Figure 10:
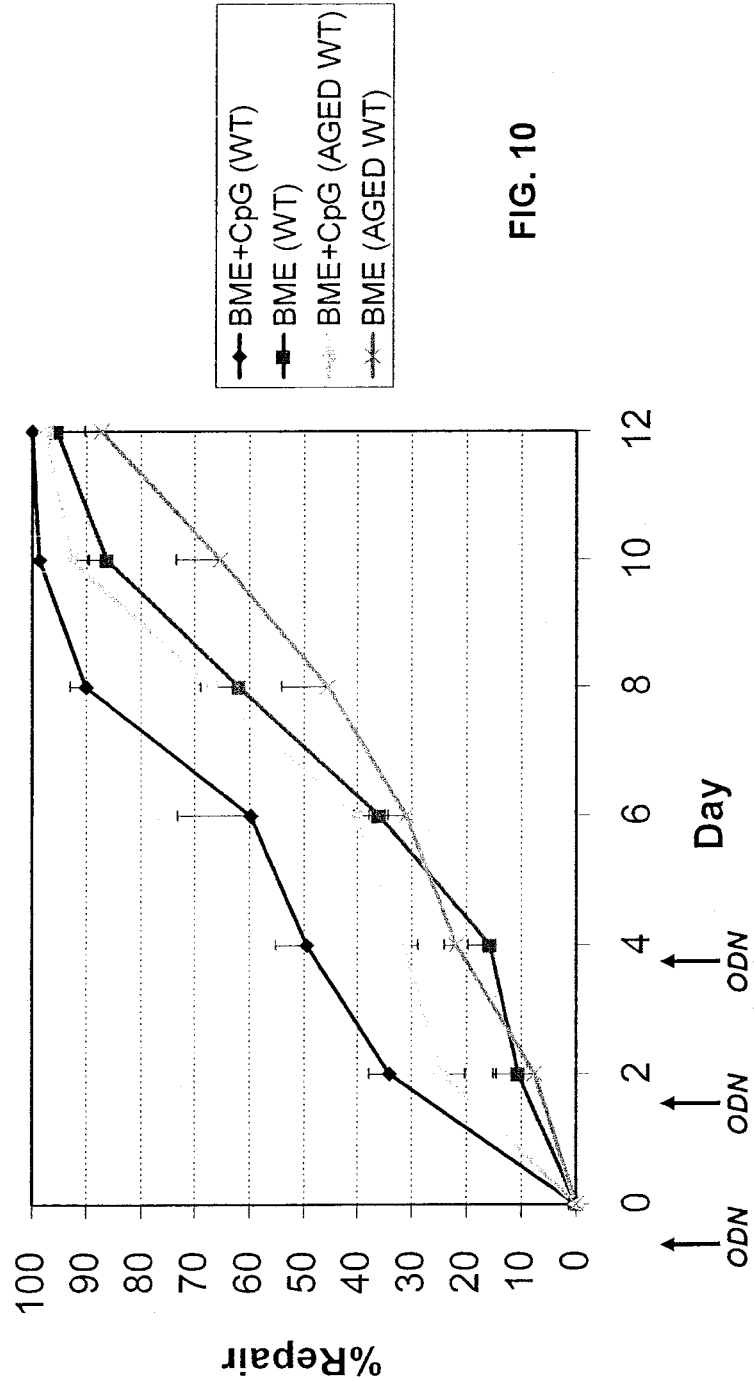
FIG. 10 a graph of results obtained in the mouse model of wound healing (see FIG. 6). In this system, CpG ODNs were administered at day 0, 2 and 4. The results are the mean percent repair at each time point. The results obtained both in young mice and aged mice are shown for comparison.
Figure 11:
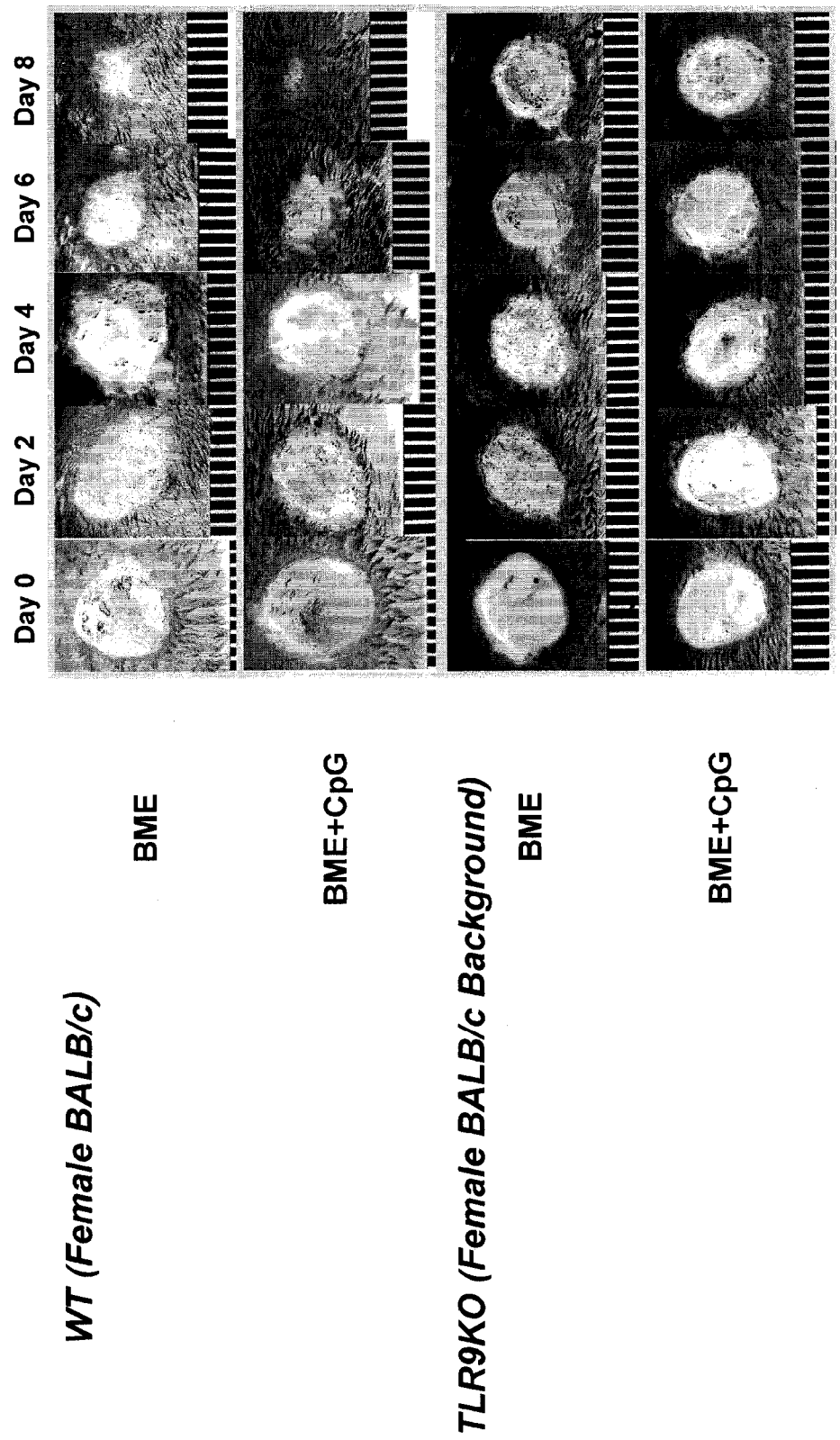
FIG. 11 is a set of digital images showing the effect of CpG-basal membrane extract (BME) gel on wound healing. Results are shown in wild-type mice and in Toll-like receptor 9 (TLR9) receptor knock out mice. The results obtained with BME alone are also shown as a control.

The results obtained from six animals (three treated with BME including K ODN and three treated with BME alone) is shown in FIG. 7. The mean percent repair in the two groups is shown in FIG. 8. There was a statistically significant difference between the treatment groups: CpG ODN accelerated wound healing by 38%. This study was repeated in animals who were more than 16 months old (see FIG. 9). The inclusion of K ODN in the BME accelerated wound healing in both young and aged animals. A comparison of the results obtained in both young and old animals is shown in FIG. 10. The inclusion of K ODN accelerated wound healing in both young and old animals. The experiment was repeated in mice deficient for the production of Toll-like receptor 9 (TLR9). Specifically, wounds were induced in wild-type mice or TLR9 knock-out mice as described above. As expected (based on the initial results described above) wound healing was accelerated in wild type mice when K ODN was included in the BME. However, wound healing was delayed in the TLR knock-out mice, indicating that this receptor was important in the uptake of K ODN for wound healing. Indeed, in TLR9 knockout mice, the wound healed at the same rate, in the presence of K ODN and in the absence of K ODN in the BME.

Example 4

CpG DNA Stimulates VEGF Expression In Vitro

In order to determine if CpG DNA directly induced cells resulted in the production of VEGF, the J774A.1 murine macrophage cell line (which is known to produce VEGF when infected with HSV) was treated in vitro with 1-3 µg of HSV-DNA or herring sperm DNA, CpG or control ODN. In these experiments, mRNA encoding the 120 isotype of VEGF was up-regulated within 3 hours of treatment with CpG but not control ODN. By 6 hours, expression of both the 120 and 164 isoforms of VEGF was induced by CpG ODN. In contrast, cells cultured in medium alone, or with control ODN, expressed minimal levels of VEGF mRNA.

A second series of experiments measured the production of VEGF protein by J774A.1 cells stimulated with CpG ODN. Fewer than 0.3% of untreated J774A.1 cells scored positive for VEGF protein (Table 2). The number of VEGF expressing cells increased within 6 hours of CpG ODN stimulation, with 20-26% of cells treated with 3 μg/ml CpG ODN producing protein at 24 hours (Table 2).

TABLE 2

Expression of VEGF following exposure of J774A.1 cells to CpG DNA

| Treatment | Dose (ug/ml) | % VEGF positive cells | |
|---|---|---|---|
| | | 6 h | 24 h |
| CpG ODN | 0.1 | 0.3 | 1.2 |
| | 1.0 | 9.1 | 21.7 |
| | 3.0 | 10.1 | 26.2 |
| | 8.0 | 12.6 | 15.3 |
| Control ODN | 3.0 | 4.5 | 5.3 |
| Media | | 0.1 | 0.3 |

J774A.1 cells were treated in vitro with 0.1-8.0 ug/ml of CpG ODN for 6 or 24 h. Cells expressing VEGF were identified by staining with rat-anti- mVEGF antibody (Ab). Results are representative of three independent experiments.

This significantly exceeded the number of cells triggered to produce VEGF by control ODN. To determine whether VEGF production correlated with CpG ODN uptake, cultures were stimulated with fluorescein-labeled CpG ODN and simultaneously monitored for VEGF expression. All VEGF producing cells stained positive for CpG ODN, suggesting that CpG DNA directly triggered these cells to produce this angiogenic protein.

This disclosure provides methods for stimulating epithelial cell growth using K ODN. The disclosure further provides methods for inducing wound healing using K ODN. In addition, a model system is provided for determining if agents inhibits epithelial cell growth. It will be apparent that the precise details of the methods described may be varied or modified without departing from the spirit of the described invention. We claim all such modifications and variations that fall within the scope and spirit of the claims below.

The invention claimed is:

1. A method of inducing epithelial cell growth, comprising contacting an epithelial cell with an effective amount of a CpG oligodeoxynucleotide, wherein the CpG oligodeoxynucleotide comprises a nucleic acid sequence as set forth as:

$$5'\ N_1N_2N_3D\text{-}CpG\text{-}WN_4N_5N_6\ 3'\quad (SEQ\ ID\ NO:\ 2)$$

wherein the central CpG motif is unmethylated, D is T, G or A, W is A or T, and $N_1$, $N_2$, $N_3$, $N_4$, $N_5$, and $N_6$ are any nucleotides and wherein the CpG oligodeoxynucleotide is 10 to 30 nucleotides in length, thereby inducing the epithelial cell growth, wherein the epithelial cell is in a graft.

2. The method of claim 1, wherein the graft is a skin graft.

3. A method of promoting wound healing in a subject, comprising selecting a subject with a wound; and administering to the subject a therapeutically effective amount of at least two CpG oligodeoxynucleotides, wherein the at least two CpG oligodeoxynucleotides each have a different nucleic acid sequence and wherein each of the at least two CpG oligodeoxynucleotides comprises a nucleic acid sequence as set forth as:

```
5' N₁N₂N₃D-CpG-WN₄N₅N₆ 3'       (SEQ ID NO: 2)
``` wherein the central CpG motif is unmethylated, D is T, G or A, W is A or T, and $N_1$, $N_2$, $N_3$, $N_4$, $N_5$, and $N_6$ are any nucleotides and wherein the CpG oligodeoxynucleotide is 10 to 30 nucleotides in length, thereby promoting wound healing in the subject.

4. The method of claim 3, wherein one of the at least two CpG oligodeoxynucleotides comprises the nucleic acid sequence set forth as SEQ ID NO: 11.

5. A method of promoting healing of a surgical wound in a subject, comprising
selecting a subject that has a surgical wound; and
administering to the subject a therapeutically effective amount of at least one CpG oligodeoxynucleotide, wherein the at least one CpG oligodeoxynucleotide comprises a nucleic acid sequence as set forth as:

```
5' N₁N₂N₃D-CpG-WN₄N₅N₆ 3'       (SEQ ID NO: 2)
``` wherein the central CpG motif is unmethylated, D is T, G or A, W is A or T, and $N_1$, $N_2$, $N_3$, $N_4$, $N_5$, and $N_6$ are any nucleotides and wherein the CpG oligodeoxynucleotide is 10 to 30 nucleotides in length, thereby promoting healing of the surgical wound in the subject.

6. The method of claim 5, wherein the subject is a transplant recipient.

7. The method of claim 4, wherein another of the at least two CpG oligodeoxynucleotides comprises the nucleic acid sequence set forth as SEQ ID NO: 12.

8. The method of claim 7, further comprising administering to the subject a therapeutically effective amount of a K-type CpG oligodeoxynucleotide comprising the nucleic acid sequence set forth as SEQ ID NO: 29.

9. The method of claim 5, wherein the subject is human.

10. A method of inducing epithelial cell Growth, comprising contacting the epithelial cell with an effective amount of at least two CpG oligodeoxynucleotides, wherein the at least two CpG oligodeoxynucleotides each have a different nucleic acid sequence, and wherein each of the CpG oligodeoxynucleotides comprises a nucleic acid sequence as set forth as:

```
5' N₁N₂N₃D-CpG-WN₄N₅N₆ 3'       (SEQ ID NO: 2)
``` wherein the central CpG motif is unmethylated, D is T, G or A, W is A or T, and $N_1$, $N_2$, $N_3$, $N_4$, $N_5$, and $N_6$ are any nucleotides and wherein each of the CpG oligodeoxynucleotide is 10 to 30 nucleotides in length, thereby inducing the epithelial cell growth, wherein the epithelial cell is in vitro.

11. The method of claim 10, wherein the epithelial cell is a human epithelial cell.

12. The method of claim 10, wherein at least one nucleotide separates any consecutive CpGs in the oligodeoxynucleotide;
$N_3D$ is selected from the group consisting of GpT, GpG, GpA, ApT and ApA; and
$WN_4$ is selected from the group consisting of TpT or CpT; and
$N_1+N_2$ is from about 0-26 bases.

13. The method of claim 5, wherein the CpG oligodeoxynucleotide is administered locally.

14. The method of claim 5, wherein the CpG oligodeoxynucleotide is administered with a basal membrane extract.

15. The method of claim 5, wherein the subject is an adult human.

16. The method of claim 5, wherein at least one nucleotide separates any consecutive CpGs in the oligodeoxynucleotide;
$N_3D$ is selected from the group consisting of GpT, GpG, GpA, ApT and ApA; and
$WN_4$ is selected from the group consisting of TpT or CpT; and
$N_1+N_2$ is from about 0-26 bases.

17. The method of claim 5, comprising administering to the subject a therapeutically effective amount of a CpG oligodeoxynucleotide comprising the nucleic acid sequence set forth as either SEQ ID NO: 11 or the nucleic acid sequence set forth as SEQ ID NO: 30.

18. The method of claim 3, wherein the at least two CpG oligodeoxynucleotides are administered locally.

19. The method of claim 3, wherein the at least two CpG oligodeoxynucleotides are administered with a basal membrane extract.

20. The method of claim 3, wherein the subject is an adult human.

21. The method of claim 3, wherein
at least one nucleotide separates any consecutive CpGs in the at least two CpG oligodeoxynucleotide;
$N_3D$ is selected from the group consisting of GpT, GpG, GpA, ApT and ApA; and
$WN_4$ is selected from the group consisting of TpT or CpT; and
$N_1+N_2$ is from about 0-26 bases.

22. The method of claim 3, comprising administering to the subject a therapeutically effective amount of a CpG oligodeoxynucleotide comprising the nucleic acid sequence set forth as either SEQ ID NO: 11 or the nucleic acid sequence set forth as SEQ ID NO: 30.

23. The method of claim 6, wherein the CpG oligodeoxynucleotide is administered locally.

24. The method of claim 6, wherein the CpG oligodeoxynucleotide is administered with a basal membrane extract.

25. The method of claim 6, wherein the subject is an adult human.

26. The method of claim 6, wherein at least one nucleotide separates any consecutive CpGs in the oligodeoxynucleotide;
$N_3D$ is selected from the group consisting of GpT, GpG, GpA, ApT and ApA; and
$WN_4$ is selected from the group consisting of TpT or CpT; and
$N_1+N_2$ is from about 0-26 bases.

27. The method of claim 6, comprising administering to the subject a therapeutically effective amount of a CpG oligodeoxynucleotide comprising the nucleic acid sequence set forth as either SEQ ID NO: 11 or the nucleic acid sequence set forth as SEQ ID NO: 30.

28. The method of claim 1, further comprising contacting the epithelial cell with an effective amount of a CpG oligodeoxynucleotide comprising the nucleic acid sequence set forth as SEQ ID NO: 12.

29. The method of claim 28, further comprising contacting the epithelial cell with an effective amount of a CpG oligodeoxynucleotide comprising the nucleic acid sequence set forth as SEQ ID NO: 29.

30. The method of claim 1, wherein the CpG oligodeoxynucleotide comprises the nucleic acid sequence set forth as SEQ ID NO: 12.

31. The method of claim 5, further comprising administering to the subject a therapeutically effective amount of a CpG oligodeoxynucleotide comprising the nucleic acid sequence set forth as SEQ ID NO: 29.

32. The method of claim 10, wherein one of the at least two CpG oligodeoxynucleotides comprises the nucleic acid sequence set forth as one of SEQ ID NOs: 3-31.

33. The method of claim 3, wherein one of the at least two CpG oligodeoxynucleotides comprises the nucleic acid sequence set forth as one of SEQ ID NOs: 3-31.

34. The method of claim 5, wherein the CpG oligodeoxynucleotide comprises the nucleic acid sequence set forth as one of SEQ ID NOs: 3-31.

35. The method of claim 6, wherein the CpG oligodeoxynucleotide comprises the nucleic acid sequence set forth as one of SEQ ID NOs: 3-31.

36. The method of claim 1, wherein the CpG oligodeoxynucleotide comprises the nucleic acid sequence set forth as SEQ ID NO: 11.

37. The method of claim 10, wherein the epithelial cell is a lung epithelial cell.

38. The method of claim 1, wherein the epithelial cell is a human epithelial cell.

39. The method of claim 5, further comprising administering to the subject a therapeutically effective amount of a CpG oligodeoxynucleotide comprising the nucleic acid sequence set forth as SEQ ID NO: 12.

40. The method of claim 10, wherein one of the at least two CpG oligodeoxynucleotides comprises the nucleic acid sequence set forth as SEQ ID NO: 11.

41. The method of claim 1, wherein the CpG oligodeoxynucleotide is administered locally in the graft.

42. The method of claim 1, wherein at least one nucleotide separates any consecutive CpGs in the at least two oligodeoxynucleotides;

$N_3D$ is selected from the group consisting of GpT, GpG, GpA, ApT and ApA; and $WN_4$ is selected from the group consisting of TpT or CpT; and $N_1+N_2$ is from about 0-26 bases.

43. The method of claim 1, wherein the CpG oligodeoxynucleotide comprises the nucleic acid sequence set forth as one of SEQ ID NOs: 3-31.

44. The method of claim 1, wherein the CpG oligodeoxynucleotide is administered with a basal membrane extract.

* * * * *

SEQUENCE LISTING

```
<160> NUMBER OF SEQ ID NOS: 33

<210> SEQ ID NO 1
<211> LENGTH: 32
<212> TYPE: DNA
<213> ORGANISM: Artificial sequence
<220> FEATURE:
<223> OTHER INFORMATION: Synthetic D-type oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (13)..(22)
<223> OTHER INFORMATION: n is a, c, g, or t or no nucleotide
<220> FEATURE:
<221> NAME/KEY: misc_feature
<222> LOCATION: (27)..(32)
<223> OTHER INFORMATION: n is g or no nucleotide

<400> SEQUENCE: 1
nnnrycgryn nnnnnnnnnn nnggggnnnn nn                               32

<210> SEQ ID NO 2
<211> LENGTH: 10
<212> TYPE: DNA
<213> ORGANISM: Artificial sequence
<220> FEATURE:
<223> OTHER INFORMATION: Synthetic K-type oligodeoxynucleotide
<220> FEATURE:
<221> NAME/KEY: misc_feature
<222> LOCATION: (1)..(3)
<223> OTHER INFORMATION: n is a, c, g, or t
```

```
<220> FEATURE:
<221> NAME/KEY: misc_feature
<222> LOCATION: (8)..(10)
<223> OTHER INFORMATION: n is a, c, g, or t

<400> SEQUENCE: 2 nnndcgwnnn                                                            10

<210> SEQ ID NO 3
<211> LENGTH: 20
<212> TYPE: DNA
<213> ORGANISM: Artificial sequence
<220> FEATURE:
<223> OTHER INFORMATION: Synthetic K-type oligodeoxynucleotide

<400> SEQUENCE: 3
ataatcgacg ttcaagcaag                                                 20

<210> SEQ ID NO 4
<211> LENGTH: 13
<212> TYPE: DNA
<213> ORGANISM: Artificial sequence
<220> FEATURE:
<223> OTHER INFORMATION: Synthetic K-type oligodeoxynucleotide

<400> SEQUENCE: 4
ctcgagcgtt ctc                                                        13

<210> SEQ ID NO 5
<211> LENGTH: 14
<212> TYPE: DNA
<213> ORGANISM: Artificial sequence
<220> FEATURE:
<223> OTHER INFORMATION: Synthetic K-type oligodeoxynucleotide

<400> SEQUENCE: 5
tctcgagcgt tctc                                                       14

<210> SEQ ID NO 6
<211> LENGTH: 16
<212> TYPE: DNA
<213> ORGANISM: Artificial sequence
<220> FEATURE:
<223> OTHER INFORMATION: Synthetic K-type oligodeoxynucleotide

<400> SEQUENCE: 6
actctggagc gttctc                                                     16

<210> SEQ ID NO 7
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 7
tgcagcgttc tc                                                         12

<210> SEQ ID NO 8
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 8
tcgaggcttc tc                                                         12
```

```
<210> SEQ ID NO 9
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 9
gtcggcgttg ac                                                         12

<210> SEQ ID NO 10
<211> LENGTH: 19
<212> TYPE: DNA
<213> ORGANISM: Artificial sequence
<220> FEATURE:
<223> OTHER INFORMATION: Synthetic K-type oligodeoxynucleotide

<400> SEQUENCE: 10
tcgactctcg agcgttctc                                                  19

<210> SEQ ID NO 11
<211> LENGTH: 20
<212> TYPE: DNA
<213> ORGANISM: Artificial sequence
<220> FEATURE:
<223> OTHER INFORMATION: Synthetic K-type oligodeoxynucleotide

<400> SEQUENCE: 11
atcgactctc gagcgttctc                                                 20

<210> SEQ ID NO 12
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 12
tcgagcgttc tc                                                         12

<210> SEQ ID NO 13
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 13
gtcggcgtcg ac                                                         12

<210> SEQ ID NO 14
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 14
gtcgacgttg ac                                                         12

<210> SEQ ID NO 15
<211> LENGTH: 16
<212> TYPE: DNA
<213> ORGANISM: Artificial sequence
<220> FEATURE:
<223> OTHER INFORMATION: Synthetic K-type oligodeoxynucleotide
```

-continued

```
<400> SEQUENCE: 15
actctcgagg gttctc                                                        16

<210> SEQ ID NO 16
<211> LENGTH: 16
<212> TYPE: DNA
<213> ORGANISM: Artificial sequence
<220> FEATURE:
<223> OTHER INFORMATION: Synthetic K-type oligodeoxynucleotide

<400> SEQUENCE: 16
actctcgagc gttctc                                                        16

<210> SEQ ID NO 17
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 17
gtcgtcgatg ac                                                            12

<210> SEQ ID NO 18
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 18
gtcgacgctg ac                                                            12

<210> SEQ ID NO 19
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 19
gtcgacgtcg ac                                                            12

<210> SEQ ID NO 20
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 20
gtcatcgatg ca                                                            12

<210> SEQ ID NO 21
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 21
gtcagcgtcg ac                                                            12
```

```
<210> SEQ ID NO 22
<211> LENGTH: 11
<212> TYPE: DNA
<213> ORGANISM: Artificial sequence
<220> FEATURE:
<223> OTHER INFORMATION: Synthetic K-type oligodeoxynucleotide

<400> SEQUENCE: 22
tcgagcgttc t                                                          11

<210> SEQ ID NO 23
<211> LENGTH: 16
<212> TYPE: DNA
<213> ORGANISM: Artificial sequence
<220> FEATURE:
<223> OTHER INFORMATION: Synthetic K-type oligodeoxynucleotide

<400> SEQUENCE: 23
actctggagc gttctc                                                     16

<210> SEQ ID NO 24
<211> LENGTH: 16
<212> TYPE: DNA
<213> ORGANISM: Artificial sequence
<220> FEATURE:
<223> OTHER INFORMATION: Synthetic K-type oligodeoxynucleotide

<400> SEQUENCE: 24
actctcgagg gttctc                                                     16

<210> SEQ ID NO 25
<211> LENGTH: 16
<212> TYPE: DNA
<213> ORGANISM: Artificial sequence
<220> FEATURE:
<223> OTHER INFORMATION: Synthetic K-type oligodeoxynucleotide

<400> SEQUENCE: 25
actctcgagc gttcta                                                     16

<210> SEQ ID NO 26
<211> LENGTH: 16
<212> TYPE: DNA
<213> ORGANISM: Artificial sequence
<220> FEATURE:
<223> OTHER INFORMATION: Synthetic K-type oligodeoxynucleotide

<400> SEQUENCE: 26
catctcgagc gttctc                                                     16

<210> SEQ ID NO 27
<211> LENGTH: 14
<212> TYPE: DNA
<213> ORGANISM: Artificial sequence
<220> FEATURE:
<223> OTHER INFORMATION: Synthetic K-type oligodeoxynucleotide

<400> SEQUENCE: 27
actctttcgt tctc                                                       14

<210> SEQ ID NO 28
<211> LENGTH: 11
<212> TYPE: DNA
<213> ORGANISM: Artificial sequence
<220> FEATURE:
<223> OTHER INFORMATION: Synthetic K-type oligodeoxynucleotide
```

```
<400> SEQUENCE: 28
tcgagcgttc t                                                        11

<210> SEQ ID NO 29
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 29
tcgttcgttc tc                                                       12

<210> SEQ ID NO 30
<211> LENGTH: 15
<212> TYPE: DNA
<213> ORGANISM: Artificial sequence
<220> FEATURE:
<223> OTHER INFORMATION: Synthetic K-type oligodeoxynucleotide

<400> SEQUENCE: 30
gctagacgtt agcgt                                                    15

<210> SEQ ID NO 31
<211> LENGTH: 12
<212> TYPE: DNA
<213> ORGANISM: Artificial sequence
<220> FEATURE:
<223> OTHER INFORMATION: Synthetic K-type oligodeoxynucleotide

<400> SEQUENCE: 31
tcgaggcttc tc                                                       12

<210> SEQ ID NO 32
<211> LENGTH: 15
<212> TYPE: DNA
<213> ORGANISM: Artificial sequence
<220> FEATURE:
<223> OTHER INFORMATION: Synthetic control oligodeoxynucleotide

<400> SEQUENCE: 32
tagagcttag cttgc                                                    15

<210> SEQ ID NO 33
<211> LENGTH: 12
<212> TYPE: DNA
<213> ORGANISM: Artificial sequence
<220> FEATURE:
<223> OTHER INFORMATION: Synthetic control oligodeoxynucleotide

<400> SEQUENCE: 33
ttgagtgttc tc                                                       12
```